US011311191B2

(12) United States Patent
Yamanari et al.

(10) Patent No.: US 11,311,191 B2
(45) Date of Patent: Apr. 26, 2022

(54) OPHTHALMIC APPARATUS

(71) Applicant: Tomey Corporation, Nagoya (JP)

(72) Inventors: Masahiro Yamanari, Nagoya (JP);
Keiichiro Okamoto, Nagoya (JP);
Hsinyuan Chuang, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 251 days.

(21) Appl. No.: 16/580,123

(22) Filed: Sep. 24, 2019

(65) Prior Publication Data

US 2020/0100674 A1 Apr. 2, 2020

(30) Foreign Application Priority Data

Sep. 28, 2018 (JP) .............................. JP2018-185485

(51) Int. Cl.
| *A61B 3/18* | (2006.01) |
| *A61B 3/10* | (2006.01) |
| *A61B 3/103* | (2006.01) |
| *A61B 3/117* | (2006.01) |
| *A61B 3/12* | (2006.01) |

(52) U.S. Cl.
CPC .............. *A61B 3/18* (2013.01); *A61B 3/102* (2013.01); *A61B 3/103* (2013.01); *A61B 3/117* (2013.01); *A61B 3/1225* (2013.01)

(58) Field of Classification Search
CPC ........... A61B 3/18; A61B 3/102; A61B 3/103; A61B 3/117; A61B 3/1225; A61B 3/14
USPC .................................................. 351/212, 221
See application file for complete search history.

(56) References Cited

U.S. PATENT DOCUMENTS

| 9,955,866 B2* | 5/2018 | Muto ................... G02B 27/141 |
| 2007/0076217 A1 | 4/2007 | Baker et al. |
| 2012/0274904 A1* | 11/2012 | Saito .................... A61B 3/1025 351/221 |
| 2013/0003015 A1* | 1/2013 | Kurosaka ............... A61B 3/102 351/206 |
| 2013/0194581 A1* | 8/2013 | Yoshida ................. A61B 3/102 356/479 |

(Continued)

FOREIGN PATENT DOCUMENTS

| CN | 203935168 U | 11/2014 |
| EP | 1602320 A1 | 7/2005 |

(Continued)

*Primary Examiner* — Mohammed A Hasan
(74) *Attorney, Agent, or Firm* — Shumaker, Loop & Kendrick, LLP

(57) ABSTRACT

An ophthalmic apparatus may include a first light source configured to output a first light, a second light source configured to output a second light, a first interferometer configured to execute an examination of a first range using first interference light, and a second interferometer configured to execute an examination of a second range using second interference light, the second range being different from the first range. A central wavelength of the first light may be different from a central wavelength of the second light. A first optical path and a second optical path may at least partially overlap with each other, the first optical path being an optical path of the first light, and the second optical path being an optical path of the second light. The examination of the first range and the examination of the second range may be able to be executed simultaneously.

14 Claims, 20 Drawing Sheets

(56) References Cited

U.S. PATENT DOCUMENTS

| | | | |
|---|---|---|---|
| 2014/0098345 | A1 | 4/2014 | Cai et al. |
| 2015/0201833 | A1 | 7/2015 | Chong |
| 2017/0245756 | A1 | 8/2017 | Hayashi et al. |
| 2018/0279872 | A1* | 10/2018 | Okamoto ............... A61B 3/117 |

FOREIGN PATENT DOCUMENTS

| | | |
|---|---|---|
| EP | 2719324 A2 | 4/2014 |
| EP | 3210526 A1 | 8/2017 |
| EP | 3384826 A2 | 10/2018 |
| JP | 2005-348755 A | 12/2005 |
| JP | 2016-077774 A | 5/2016 |
| JP | 2017-502817 A | 1/2017 |

* cited by examiner

OPHTHALMIC APPARATUS

CROSS-REFERENCE TO RELATED APPLICATION

This application claims priority to Japanese Patent Application No. 2018-185485, filed on Sep. 28, 2018, the entire contents of which are incorporated herein by reference.

TECHNICAL FIELD

The art disclosed herein relates to an ophthalmic apparatus. Specifically, it relates to an ophthalmic apparatus configured to be capable of carrying out plural types of measurements on a subject eye.

BACKGROUND

An ophthalmic apparatus configured to measure refractive power and shapes of respective portions of the subject eye (such as an anterior segment and a retina) is being developed. Diagnosis on disorders in the subject eye and a visual function examination thereof can accurately be performed by making a comprehensive determination based on the refractive power and the shapes of the respective portions of the subject eye. In order to do so, plural types of measurements for the respective portions of the subject eye and an entirety of the subject eye are necessary, so a single ophthalmic apparatus capable of carrying out plural types of measurements is being developed. For example, Japanese Patent Application Publication No. 2016-77774 describes an ophthalmic apparatus that measures a cornea shape, a refractive power, and an eye axial length of a subject eye. The ophthalmic apparatus of Japanese Patent Application Publication No. 2016-77774 measures a shape of an anterior surface of the cornea using a kerato measurement ring, and measures the eye axial length using optical coherence. Further, Japanese Patent Application Publication No. 2017-502817 describes an ophthalmic apparatus that measures an anterior segment and a retina using optical coherence tomography (Optical Coherence Tomography: OCT). The ophthalmic apparatus of Japanese Patent Application Publication No. 2017-502817 splits light outputted from a single light source into two light having different wavelengths using a beam splitter. One of the two light is used for an anterior segment OCT measurement, and the other is used for a retinal OCT measurement.

SUMMARY

Conventional ophthalmic apparatuses indeed enable plural types of measurements, however, since each of such measurements is carried out independently, the measurement time is long and measurement efficiency for a subject eye is not sufficient. Due to this, problems, such as increased burden on the subject and decrease in measurement accuracy caused by a change in a state of the subject eye during the measurements, may arise. The disclosure herein provides art that enables plural types of measurements on a subject eye efficiently.

An ophthalmic apparatus disclosed herein may comprise a first light source configured to output first light with which a subject eye is irradiated, a second light source configured to output second light with which the subject eye is irradiated, a first interferometer configured to execute an examination of a first range of the subject eye using first interference light which is obtained from reflected light of the first light, and a second interferometer configured to execute an examination of a second range of the subject eye using second interference light which is obtained from reflected light of the second light, the second range being different from the first range. A central wavelength of the first light may be different from a central wavelength of the second light. A first optical path and a second optical path may at least partially overlap with each other, the first optical path being an optical path of the first light, and the second optical path being an optical path of the second light. The examination of the first range and the examination of the second range may be able to be executed simultaneously.

DETAILED DESCRIPTION

Figure 1:
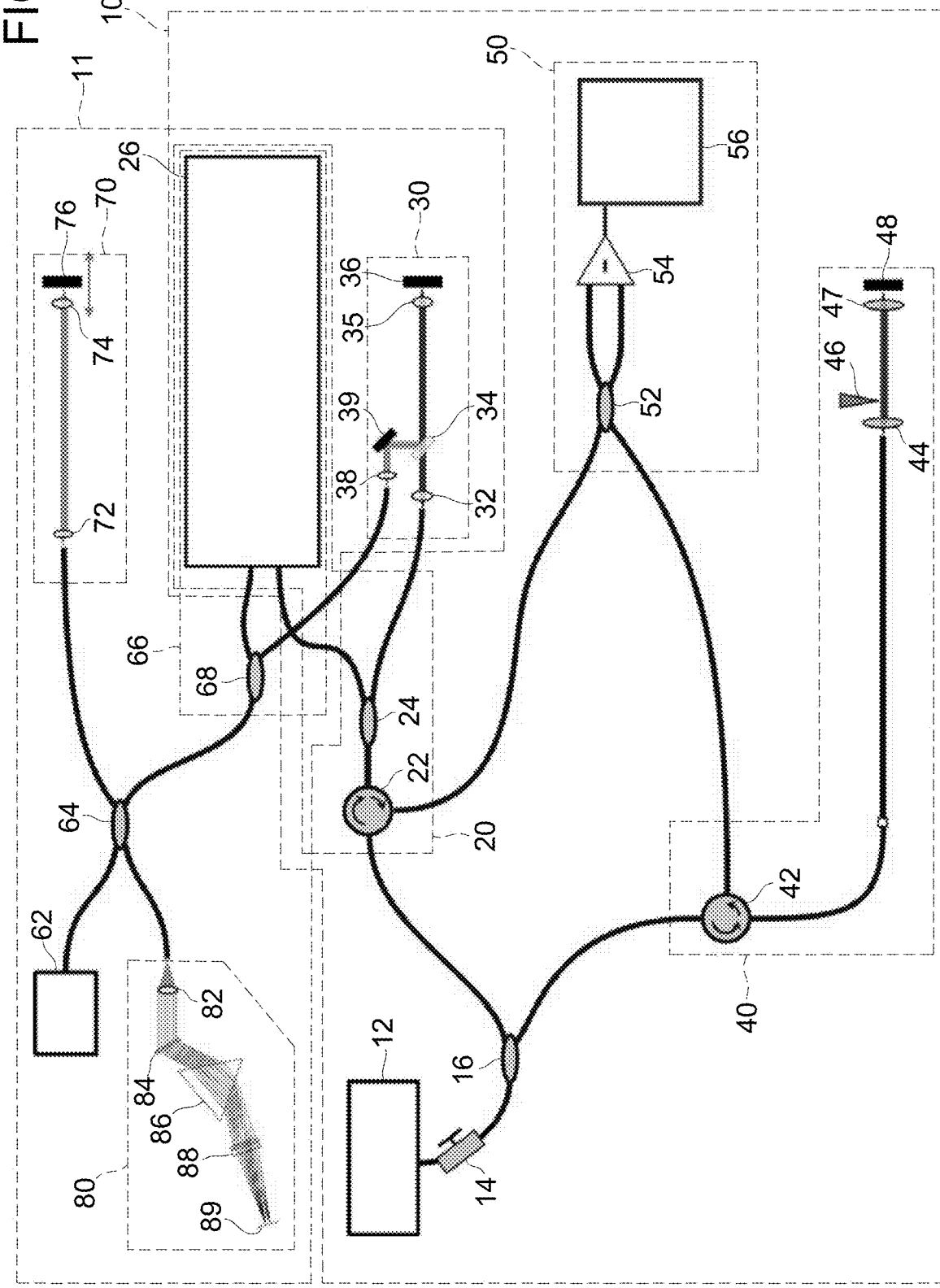
FIG. 1 shows a schematic configuration diagram of an anterior segment OCT interferometer and a retinal OCT interferometer of an ophthalmic apparatus of a first embodiment.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved ophthalmic apparatuses, as well as methods for using and manufacturing the same.

Moreover, combinations of features and steps disclosed in the following detailed description may not be necessary to practice the present disclosure in the broadest sense, and are instead taught merely to particularly describe representative examples of the present disclosure. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

Some of the features characteristic to below-described embodiments will herein be listed. It should be noted that the respective technical elements are independent of one another, and are useful solely or in combinations. The combinations thereof are not limited to those described in the claims as originally filed.

In an embodiment of the present technology, an ophthalmic apparatus may comprise a first light source configured to output first light with which a subject eye is irradiated, a second light source configured to output second light with which the subject eye is irradiated, a first interferometer configured to execute an examination of a first range of the subject eye using first interference light which is obtained from reflected light of the first light, and a second interferometer configured to execute an examination of a second range of the subject eye using second interference light which is obtained from reflected light of the second light, the second range being different from the first range. A central wavelength of the first light may be different from a central wavelength of the second light. A first optical path and a second optical path may at least partially overlap with each other, the first optical path being an optical path of the first light, and the second optical path being an optical path of the second light. The examination of the first range and the examination of the second range may be able to be executed simultaneously.

In the above ophthalmic apparatus, since the central wavelength of the first light and the central wavelength of the second light are different, the first light and the second light allow different parts of the subject eye to be irradiated with light with strong intensities. Due to this, the examination of the first range and the examination of the second range can be executed with high accuracy by setting the first light and the second light to have central wavelengths suitable for the examination of the first range and the examination of the second range. Further, the first optical path which is the optical path of the first light and the second optical path which is the optical path of the second light at least partially overlap with each other, so the subject eye can be irradiated simultaneously with the first light and the second light. As above, according to the above ophthalmic apparatus, the examinations for different ranges of the subject eye can be executed simultaneously using the first interferometer and the second interferometer. That is, in the above ophthalmic apparatus, plural types of measurements on the subject eye (that is, the examination of the first range and the examination of the second range) can be executed efficiently. Due to this, the measurement time can be shortened as compared to conventional ophthalmic apparatuses and the examinations can be executed on the subject eye under the substantially same state.

In an embodiment of the present technology, the first range may include an anterior segment of the subject eye, and the second range may include a retina of the subject eye. According to this configuration, important portions of the subject eye can suitably be examined in the ophthalmic examinations.

In an embodiment of the present technology, the central wavelength of the first light may be longer than the central wavelength of the second light, the central wavelength of the first light outputted from the first light source may be 0.95 µm or more and 1.80 µm or less, and the central wavelength of the second light outputted from the second light source may be 0.40 µm or more and 1.15 µm or less. According to this configuration, the first range and the second range can be irradiated with light having suitable wavelengths, respectively. Due to this, the examination of the first range and the examination of the second range can be executed with high accuracy.

In an embodiment of the present technology, the ophthalmic apparatus may further comprise a scanner disposed on an overlapping optical path where the first optical path and the second optical path overlap, and configured to scan the first light outputted from the first light source and scan the second light outputted from the second light source. According to this configuration, the scanner can be used to scan the first light with which the first range is irradiated as well as to scan the second light with which the second range is irradiated. This enables a configuration in the ophthalmic apparatus to avoid becoming complicated and a number of components to be reduced.

In an embodiment of the present technology, the second light source may be configured to output the second light in pulses when a scan resolution in the examination of the second range is lower than an optical resolution in the examination of the second range. In some cases, a speed for the examination of the second range may be set slower than a speed for the examination of the first range. That is, a time required for the examination of the second range may be set longer than a time required for the examination of the first range. In such a case, if the scanner scans according to the speed for the examination of the first range in the configuration where the single scanner simultaneously scans the first light and the second light, an interference signal obtained from the second interference light may attenuate due to the relatively slow speed for the examination of the second range and the examination of the second range may not be executed with high accuracy. As such, when the scan resolution in a scan direction is lower than the optical resolution in a lateral direction, the attenuation of the interference signal obtained from the second interference light can be suppressed by outputting the second light in pulses according to the speed for the examination of the second range.

In an embodiment of the present technology, the second light source may be configured to continuously output the second light when a scan resolution in the examination of the second range is higher than an optical resolution in the examination of the second range. When the scan resolution in the examination of the second range is higher than the optical resolution in the examination of the second range, the interference signal is less likely to attenuate even if the second light is continuously outputted. Due to this, by employing this configuration that continuously outputs the second light when the scan resolution in the scan direction is higher than the optical resolution in the lateral direction in the examination of the second range, the second light source can be easily controlled.

In an embodiment of the present technology, the ophthalmic apparatus may further comprise an objective lens disposed on the overlapping optical path and disposed between the scanner and the subject eye. The scanner may comprise a mirror which changes traveling directions of the first light and the second light to a predetermined direction. The second light source may be configured to output the second light in pulses when the following formula is satisfied:

$$(Fp \cdot \lambda p \cdot Mp)/Dp < (\pi/4) \cdot (Ma/f_{obj}) \cdot (Wa/Na) \cdot Fa$$

(wherein in the examination of the first range: Fa is an A-scan speed; Wa is a scan range in a first direction orthogonal to a depth direction of the subject eye; Na is a number of times of A-scans within the scan range in the first direction; and Ma is a magnification of the mirror, wherein in the examination of the second range: Fp is an A-scan speed; Mp is a magnification of the mirror, wherein $\lambda p$ is the central wavelength of the second light; Dp is a beam diameter of the second light; and $f_{obj}$ is a focal length of the objective lens.). When such a condition is satisfied, the interference signal obtained from the second interference light is likely to attenuate. Due to this, by outputting the second light in pulses, the attenuation of the interference signal can be suppressed.

In the disclosure herein, acquisition of interference signal including position information in the depth direction is termed "A-scan". The "A-scan" in the disclosure herein does not necessarily require dynamic change of a particular configuration in the ophthalmic apparatus disclosed herein. Specifically, the "A-scan" in the disclosure herein may include the following aspects. For example, the "A-scan" may include an aspect that acquires an interference signal including position information at depths in the depth direction by sweeping a wavelength or wave number of light outputted from a light source in SS-OCT (swept-source OCT), an aspect that acquires an interference signal including position information at depths in the depth direction by spectrally diffracting spectrum to decompose the same for each wavelength or for each wave number in SD-OCT (spectral-domain OCT), and an aspect that acquires an interference signal including position information at depths in the depth direction by changing an optical path length of reference light in TD-OCT (time-domain OCT). Further, in the disclosure herein, a number of times the A-scan is repeated per unit time is termed "A-scan speed". For example, in a case where the A-scan is executed 100,000 times per one second, the A-scan speed is 100 kHz.

In an embodiment of the present technology, the ophthalmic apparatus may further comprise an objective lens disposed on the overlapping optical path and disposed between the scanner and the subject eye. The scanner may comprise a mirror which changes traveling directions of the first light and the second light to a predetermined direction. The second light source may be configured to continuously output the second light when the following formula is satisfied:

$$(Fp \cdot \lambda p \cdot Mp)/Dp > (\pi/4) \cdot (Ma/f_{obj}) \cdot (Wa/Na) \cdot Fa$$

(wherein in the examination of the first range: Fa is an A-scan speed; Wa is a scan range in a first direction orthogonal to a depth direction of the subject eye; Na is a number of times of A-scans within the scan range in the first direction; and Ma is a magnification of the mirror, wherein in the examination of the second range: Fp is an A-scan speed; and Mp is a magnification of the mirror, wherein $\lambda p$ is the central wavelength of the second light, Dp is a beam diameter of the second light, and $f_{obj}$ is a focal length of the objective lens.). When such a condition is satisfied, the interference signal obtained from the second interference light less likely attenuates. Thus, by continuously outputting the second light, the second light source can be easily controlled.

In an embodiment of the present technology, the second light source may be configured to output the second light in pulses with a period 1/Fp such that a duty cycle D satisfies the following formula:

$$D < Fp/\{\pi/(4\lambda p) \cdot (Dp/f_{obj}) \cdot (Ma/Mp) \cdot (Wa/Na) \cdot Fa\}.$$

In such a configuration, the light is outputted according to the A-scan speed Fp for the subject eye in the examination of the second range, by which the attenuation of the interference signal obtained from the second interference light can suitably be suppressed. The duty cycle may be expressed as to/(to+ts), where a time during which the second light is outputted is "to" and a time during which the second light is not outputted is "ts", for example.

In an embodiment of the present technology, the ophthalmic apparatus may further comprise an objective lens disposed on the overlapping optical path and disposed between the scanner and the subject eye. The scanner may comprise a mirror which changes traveling directions of the first light and the second light to a predetermined direction. The second interferometer may be configured to detect the second light in pulses with a period 1/Fp such that a duty cycle D satisfies the following formula:

$$D < Fp/\{\pi/(4\lambda p) \cdot (Dp/f_{obj}) \cdot (Ma/Mp) \cdot (Wa/Na) \cdot Fa\}$$

(wherein in the examination of the first range: Fa is an A-scan speed; Wa is a scan range in a first direction orthogonal to a depth direction of the subject eye; Na is a number of times of A-scans within the scan range in the first direction; and Ma is a magnification of the mirror, wherein in the examination of the second range: Fp is an A-scan speed; and Mp is a magnification of the mirror, wherein $\lambda p$ is the central wavelength of the second light, Dp is a beam diameter of the second light, and $f_{obj}$ is a focal length of the objective lens.). In some cases, the speed for the examination of the second range may be set slower than the speed for the examination of the first range. That is, the time required for the examination of the second range may be set longer than the time required for the examination of the first range. In such a case, if the scanner scans according to the speed for the examination of the first range in the configuration where the first light and the second light are simultaneously scanned by the single scanner, the interference signal obtained from the second interference light may attenuate due to the relatively slow speed of the examination of the second range and the examination of the second range may not be executed with high accuracy. According to the above configuration, the second interference light is detected according to the A-scan speed Fp in the examination of the second range, by which the attenuation of the interference signal obtained from the second interference light can be suppressed. The duty cycle may be expressed as td/(td+tu), where a time during which the second light is detected is "td" and a time during which the second light is not detected is "tu", for example.

In an embodiment of the present technology, the ophthalmic apparatus may further comprise a refractive power measurement optical system configured to measure refractive power of the subject eye using the second light outputted from the second light source. According to this configuration, the light source used in the examination of the second range can be also used to measure the refractive power of the subject eye. This enables the configuration in the ophthalmic apparatus to avoid becoming complicated and the number of components to be reduced.

In an embodiment of the present technology, the first range may include an anterior segment of the subject eye, and the second range may include a retina of the subject eye. The ophthalmic apparatus may further comprise a processor storing a distance from the first range to the second range that is measured in advance, and a memory storing computer-readable instructions therein. The computer-readable instructions, when executed by the processor, may cause the processor to calculate a shape of the anterior segment of the subject eye based on the first interference light and calculate a shape of the retina of the subject eye based on the second interference light, and calculate an eye axial length of the subject eye based on the calculated shape of the anterior segment, the calculated shape of the retina, and the distance from the first range to the second range. According to this configuration, a plural types of measurements on the subject eye, including the measurement of the eye axial length, can be executed in the single ophthalmic apparatus.

In an embodiment of the present technology, the first interferometer may comprise a first calibration mirror, the second interferometer may comprise a second calibration mirror. The processor may store a first reference position of the first calibration mirror, a second reference position of the second calibration mirror, and a distance from the first reference position to the second reference position, the first reference position and the second reference position being predetermined. The computer-readable instructions, when executed by the processor, may cause the processor to calculate a first displacement amount between a current position of the first calibration mirror and the first reference position when calculating the shape of the anterior segment, calculate a second displacement amount between a current position of the second calibration mirror and the second reference position when calculating the shape of the retina, and correct the distance from the first range to the second range based on the first displacement amount and the second displacement amount when calculating the eye axial length. According to this configuration, even in a case where a difference between an optical path length of the first light in the first interferometer and an optical path length of the second light in the second interferometer changes, the distance from the first range to the second range can suitably be corrected. Thus, an accurate eye axial length can be calculated.

Representative, non-limiting examples of the present disclosure will now be described in further detail with reference to the attached drawings. This detailed description is merely intended to teach a person of skill in the art further details for practicing preferred aspects of the present teachings and is not intended to limit the scope of the present disclosure. Furthermore, each of the additional features and teachings disclosed below may be utilized separately or in conjunction with other features and teachings to provide improved ophthalmic apparatuses, as well as methods for using and manufacturing the same.

Moreover, combinations of features and steps disclosed in the following detailed description may not be necessary to practice the present disclosure in the broadest sense, and are instead taught merely to particularly describe representative examples of the present disclosure. Furthermore, various features of the above-described and below-described representative examples, as well as the various independent and dependent claims, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the compositions of the features in the embodiments and/or the claims. In addition, all value ranges or indications of groups of entities are intended to disclose every possible intermediate value or intermediate entity for the purpose of original written disclosure, as well as for the purpose of restricting the claimed subject matter.

First Embodiment

Hereinbelow, an ophthalmic apparatus 1 of a first embodiment will be described. As shown in FIG. 1, the ophthalmic apparatus 1 is provided with an anterior segment OCT interferometer 10 configured to capture tomographic images of an anterior segment of a subject eye E and a retinal OCT interferometer 11 configured to capture tomographic images of a retina of the subject eye E.

The anterior segment OCT interferometer 10 is used to capture tomographic images of the anterior segment of the subject eye E by optical coherence tomography. The anterior segment OCT interferometer 10 employs a Fourier domain scheme which performs light wave interference in a Fourier space, and especially uses swept-source OCT (SS-OCT) which captures tomographic images of the anterior segment of the subject eye E by detecting a spectrum interference signal using a wavelength scanning light source that scans light while changing its wavelength over time. As the wavelength scanning light source, for example, an external resonator-type wavelength sweeping light source that uses a wavelength-changing filter such as a diffraction grating and a prism, or various types of external resonator-type light source that uses a resonator-length changing Fabry-Perot tunable filter. Further, for example, a wavelength changeable DBR (Distributed Bragg Reflector) laser or a wavelength changeable surface emitting laser (VCSEL (Vertical Cavity Surface Emitting Laser)) that uses a MEMS (Micro Electro Mechanical Systems) mechanism may be used. Shapes of respective parts of the anterior segment of the subject eye E (such as a cornea, an anterior chamber, and a crystalline lens) can be measured from the tomographic images captured by the anterior segment OCT interferometer 10. The anterior segment OCT interferometer 10 is not limited to SS-OCT, and it may adopt, for example, another OCT using the Fourier domain scheme (such as spectrum domain OCT) or a scheme other than the Fourier domain scheme (such as time domain scheme).

As shown in FIG. 1, the anterior segment OCT interferometer 10 is provided with an anterior segment light source 12, a measurement optical system 20, a calibration optical system 30, a reference optical system 40, and an interference optical system 50.

The anterior segment light source 12 is a wavelength sweeping light source, and a wavelength (wave number) of light outputted therefrom changes with a predetermined period. The anterior segment light source 12 is configured to output light with a long wavelength and is capable of outputting light with a central wavelength of 0.95 µm or more and 1.80 µm or less, for example. In the present embodiment, the anterior segment light source 12 outputs light with a central wavelength of 1.31 µm. When light with a long wavelength is used, it becomes easier for the light to pass through strong-scattering tissues such as opacity of the crystalline lens, a ciliary body, a conjunctiva, and a sclera, and further, due to its large absorbance by water, the light is less likely to reach the retina, which allows stronger light to be irradiated. Due to this, by outputting the light with the central wavelength of 0.95 µm or more from the anterior segment light source 12, the chance of the light reaching the tissues constituted of scattering substances can be increased. Further, since the light with the central wavelength of 0.95 µm or more and 1.80 µm or less is not dispersed much by water, anterior segment OCT images with high image quality can be acquired by irradiating the subject eye E with the light within this range. Further, by outputting the light with the central wavelength of 1.80 µm or less from the anterior segment light source 12, a target site can be measured with high sensitivity by an indium/gallium/arsenic (InGaAs)-based light receiving element. Thus, by outputting the light of 0.95 µm or more and 1.80 µm or less from the anterior segment light source 12, the tomographic images of the anterior segment of the subject eye E can suitably be captured.

The anterior segment light source 12 has a polarization controller 14 and an optical coupler 16 connected thereto. Thus, the light outputted from the anterior segment light source 12 is inputted to the optical coupler 16 through the polarization controller 14 and is split in the optical coupler 16 into measurement light and reference light, for example, at a ratio of 9:1, and these light are inputted respectively to the measurement optical system 20 and the reference optical system 40.

The measurement optical system 20 is provided with an optical circulator 22, an optical coupler 24, and a probe optical system 26. The measurement light inputted to the measurement optical system 20 from the anterior segment light source 12 is inputted to the optical circulator 22. The measurement light inputted to the optical circulator 22 is inputted to the optical coupler 24 and is split in the optical coupler 24, for example, at a ratio of 99:1, and these lights are inputted respectively to the probe optical system 26 and the calibration optical system 30.

Figure 2:
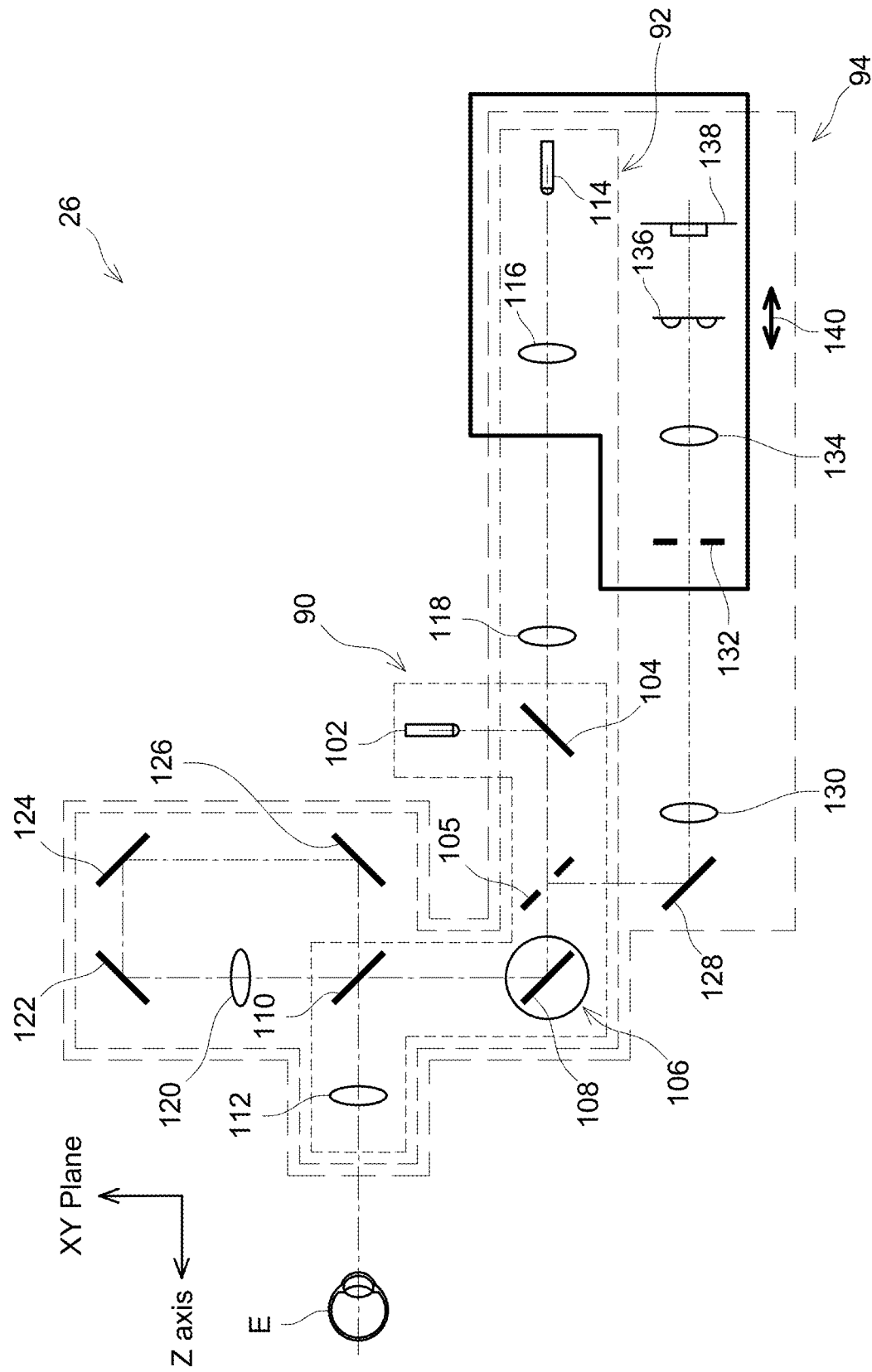
FIG. 2 shows a schematic configuration diagram of a probe optical system of the ophthalmic apparatus of the first embodiment.

As shown in FIG. 2, the probe optical system 26 is provided with an anterior segment OCT optical system 90 configured to capture tomographic images of the anterior segment of the subject eye E, a retinal OCT optical system 92 configured to capture tomographic images of the retina of the subject eye E, a refraction measurement optical system 94 configured to measure refractive power of the subject eye E, an alignment optical system (not shown) configured to align the ophthalmic apparatus 1 in a predetermined positional relationship with respect to the subject eye E, and an observation optical system (not shown) configured to observe the subject eye E. For the alignment optical system and the observation optical system, those used in known ophthalmic apparatuses can be used, thus detailed descriptions thereof will be omitted. The retinal OCT optical system 92 and the refraction measurement optical system 94 will be described later.

The anterior segment OCT optical system 90 is provided with a fiber collimator 102, dichroic mirrors 104, 110, a mirror 105 having a hole at a center thereof (hereinbelow termed a perforated mirror 105), a scanner 106, and an objective lens 112. The light inputted from the optical coupler 24 to the probe optical system 26 (that is, the anterior segment OCT optical system 90) is emitted from the fiber collimator 102 and is provided to the dichroic mirror 104. The dichroic mirror 104 is configured to reflect light with a longer wavelength than 0.90 µm and allow light with a shorter wavelength than 0.90 µm to penetrate therethrough. Since the light outputted from the anterior segment light source 12 has the central wavelength of 1.31 µm, it is reflected by the dichroic mirror 104. The light reflected on the dichroic mirror 104 passes through the circular hole at the center of the perforated mirror 105 and is provided to the scanner 106. The scanner 106 is, for example, a galvanometer, and a traveling direction of the light is changed to a predetermined direction by a Galvano mirror 108 attached to the galvanometer. The light emitted from the scanner 106 is provided to the dichroic mirror 110. The dichroic mirror 110 is configured to reflect light with a longer wavelength than 0.90 µm and allow light with a shorter wavelength than 0.90 µm to penetrate therethrough. Since the light emitted from the scanner 106 has the central wavelength of 1.31 µm, it is reflected by the dichroic mirror 110. Then, the anterior segment of the subject eye E (such as the cornea, anterior chamber, and crystalline lens) is irradiated with the light reflected on the dichroic mirror 110 through the objective lens 112. The measurement light reflected on the anterior segment of the subject eye E is inputted to the fiber collimator 102 through the objective lens 112, the dichroic mirror 110, the scanner 106, the perforated mirror 105, and the dichroic mirror 104. Then, as shown in FIG. 1, it is inputted again to the optical circulator 22 through the optical coupler 24. The measurement light inputted to the optical circulator 22 is inputted to an optical coupler 52 of the interference optical system 50.

The light split in the optical coupler 24 of the measurement optical system 20 is inputted to the calibration optical system 30 as described above. As shown in FIG. 1, the calibration optical system 30 is provided with lenses 32, 35, 38, a dichroic mirror 34, a mirror 39, and a calibration mirror 36. The light inputted to the calibration optical system 30 from the optical coupler 24 is emitted from a fiber collimator that is not shown, and is provided to the dichroic mirror 34 through the lens 32. The dichroic mirror 34 is configured to allow light with a longer wavelength than 0.90 µm to penetrate therethrough and reflect light with a shorter wavelength than 0.90 µm. Since the light emitted from the fiber collimator (not shown) has a central wavelength longer than 0.90 µm (that is, 1.31 µm), it penetrates through the dichroic mirror 34. The light that penetrated through the dichroic mirror 34 is inputted to the calibration mirror 36 through the lens 35. Calibration light reflected by the calibration mirror 36 is inputted again to the fiber collimator through the lens 35, the dichroic mirror 34, and the lens 32, and then is inputted to the optical circulator 22 through the optical coupler 24. The calibration light inputted to the optical circulator 22 is inputted to the optical coupler 52 of the interference optical system 50. The lens 38 and the mirror 39 of the calibration optical system 30 are used in the retinal OCT interferometer 11 to be described later.

The reference light that is split in the optical coupler 16 is inputted to the reference optical system 40 as described above. The reference optical system 40 is provided with an optical circulator 42, lenses 44, 47, an attenuator 46, and a reference mirror 48. The reference light inputted from the anterior segment light source 12 to the reference optical system 40 is inputted to the optical circulator 42. The reference light inputted to the optical circulator 42 is emitted from a fiber collimator that is not shown and is inputted to the reference mirror 48 through the lenses 44, 47. An optical path length of the reference light outputted from the anterior segment light source 12 is adjusted by a zero-point adjusting mechanism (not shown). For the zero-point adjusting mechanism, those used in known ophthalmic apparatuses can be used, thus a detailed description thereof will be omitted. The reference light reflected by the reference mirror 48 is inputted again to the fiber collimator and then is inputted to the optical circulator 42. The reference light inputted to the optical circulator 42 is inputted to the optical coupler 52 of the interference optical system 50.

The interference optical system 50 is provided with the optical coupler 52, a light receiving element 54, and a signal processor 56. In the optical coupler 52, the measurement light reflected from the subject eye E and the reference light generated by the reference optical system 40 are combined, and the combined measurement interference light is inputted to the light receiving element 54. Further, in the optical coupler 52, the calibration light generated by the calibration optical system 30 and the reference light generated by the reference optical system 40 are combined, and the combined calibration interference light is inputted to the light receiving element 54. An InGaAs-based element may be used as the light receiving element 54, for example, and interference of the measurement interference light and the calibration interference light is measured for each wavelength in the light receiving element 54. Further, an interference signal corresponding to an intensity of the measured interference light is inputted to the signal processor 56. The signal processor 56 is configured to sample the acquired interference signal. Known data collection devices (so-called DAQs) may be used as the signal processor 56. The sampled interference signal is inputted to a processor 200 to be described later. The processor 200 is configured to execute Fourier transform processing and the like on the interference signal, by which tomographic images of the anterior segment along scan lines are acquired.

Figure 3:
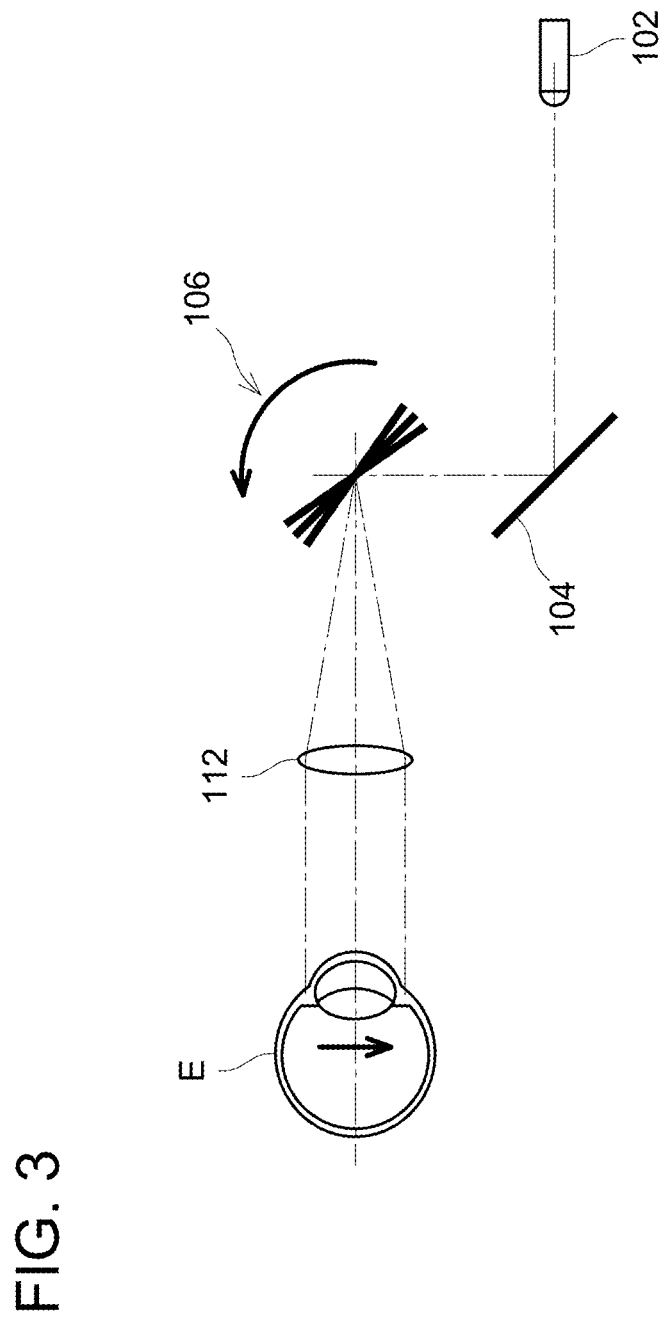
FIG. 3 is a diagram schematically showing an optical path of light in an anterior segment OCT optical system.

Scan in the anterior segment OCT optical system 90 will be described with reference to FIG. 3. FIG. 3 shows an optical path along which the light emitted from the fiber collimator 102 reaches the subject eye E. FIG. 3 shows only some of optical members disposed on the optical path (that is, the dichroic mirror 104, the scanner 106, and the object lens 112) and omits the other optical members. As shown in FIG. 3, in the anterior segment OCT optical system 90, the scanner 106 is disposed at a posterior focal point of the object lens 112. Due to this, the light scanned by the scanner 106 is provided to the subject eye E in parallel to an optical axis. That is, telecentric scan is executed in the anterior segment OCT optical system 90, and tomographic images of the subject eye E without distortion can be acquired. Further, an end surface of the fiber collimator 102 is disposed at a position conjugate with the anterior segment of the subject eye E. Due to this, the light emitted from the fiber collimator 102 can be concentrated to the anterior segment of the subject eye E. Thus, the anterior segment OCT optical system 90 can suitably capture tomographic images of the anterior segment of the subject eye E.

Next, the retinal OCT interferometer 11 will be described. The retinal OCT interferometer 11 is used to capture images of the retina of the subject eye E by optical coherence tomography. The retinal OCT interferometer 11 employs the Fourier domain scheme which performs light wave interference in a Fourier space, and especially uses spectrum domain OCT (SD-OCT) which captures tomographic images of the retina of the subject eye E by detecting spectrum information using a fixed wavelength light source that outputs light with a wide-band wavelength and a spectrometer. Shapes of respective parts of the retina of the subject eye E (such as the retina and choroid) can be measured from the tomographic images captured by the retinal OCT interferometer 11. The retinal OCT interferometer 11 is not limited to the SD-OCT, and may use, for example, another OCT using the Fourier domain scheme (such as SS-OCT) or a scheme other than the Fourier domain scheme (such as time-domain scheme).

As shown in FIG. 1, the retinal OCT interferometer 11 is provided with a retina light source 62, a measurement optical system 66, the calibration optical system 30, a reference optical system 70, and an interference optical system 80.

The retina light source 62 is a fixed wavelength-type light source. The retina light source 62 is configured to output light having a central wavelength that differs from that of the light outputted from the anterior segment light source 12, and is capable of outputting light with a central wavelength of 0.40 µm or more and 1.15 µm or less, for example. Further, for example, the retina light source 62 may be configured to output light having a half width in a wavelength range that differs from a wavelength range of a half width of the light outputted by the anterior segment light source 12. In this embodiment, the retina light source 62 outputs light with a central wavelength of 0.83 µm. The light with the central wavelength of 0.40 µm or more and 1.15 µm or less has a high intraocular penetration rate. Due to this, by outputting the light with the central wavelength of 0.40 µm or more and 1.15 µm or less from the light source, the light can sufficiently be provided to the retina of the subject eye E. Further, silicon-based light receiving elements has a high sensitivity to light with the central wavelength of 0.40 µm or more and 0.95 µm or less. Further, light with the central wavelength of 0.95 µm or more and 1.15 µm or less is not dispersed much by water, thus retinal OCT images with high quality can be acquired by irradiating the subject eye E with light in that range. Thus, by outputting the light with the central wavelength of 0.40 µm or more and 1.15 µm or less from the light source, the tomographic images of the retina of the subject eye E can suitably be captured.

An optical coupler 64 is connected to the retina light source 62. As such, light outputted from the retina light source 62 is inputted to the optical coupler 64 and is split in the optical coupler 64 into measurement light and reference light, for example, at a ratio of 9:1, and these light are respectively inputted to the measurement optical system 66 and the reference optical system 70.

The measurement optical system 66 is provided with an optical coupler 68 and the probe optical system 26. The measurement light inputted from the retina light source 62 to the measurement optical system 66 is inputted to the optical coupler 68 and is split in the optical coupler 68, for example, at a ratio of 99:1, and these light are inputted respectively to the probe optical system 26 and the calibration optical system 30.

As shown in FIG. 2, the retinal OCT optical system 92 of the probe optical system 26 is provided with a fiber collimator 114, lenses 116, 118, 120, the dichroic mirrors 104, 110, the perforated mirror 105, the scanner 106, mirrors 122, 124, 126, and the objective lens 112. The light inputted from the optical coupler 68 to the probe optical system 26 (that is, to the retina OCT optical system 92) is emitted from the fiber collimator 114, and is provided to the dichroic mirror 104 through the lenses 116, 118. As described above, the dichroic mirror 104 allows light with the wavelength shorter than 0.90 μm to penetrate therethrough, so the light outputted from the retina light source 62 (having the central wavelength of 0.83 μm) penetrates through the dichroic mirror 104. Here, an optical path of the retinal OCT optical system 92 overlaps with the optical path of the anterior segment OCT optical system 90.

The light that penetrated through the dichroic mirror 104 passes through the circular hole at the center of the perforated mirror 105 and is provided to the scanner 106. A traveling direction of the light provided to the scanner 106 is changed to the predetermined direction, and the light is provided to the dichroic mirror 110. As described above, since the dichroic mirror 110 allows light with the wavelength shorter than 0.90 μm to penetrate therethrough, the light having passed through the lens 118 (with the central wavelength of 0.83 μm) penetrates the dichroic mirror 110. Here, the optical path of the retinal OCT optical system 92 becomes an optical path which differs from the optical path of the anterior segment OCT optical system 90 again.

The light that penetrated through the dichroic mirror 110 passes through the lens 120 and is reflected by the mirrors 122, 124, 126. The light reflected on the mirror 126 is again provided to the dichroic mirror 110 and penetrates through the dichroic mirror 110 as described above. Here, the optical path of the retinal OCT optical system 92 overlaps with that of the anterior segment OCT optical system 90 again. The retina of the subject eye E (such as the retina and choroid) is irradiated with the light that has penetrated through the dichroic mirror 110, through the objective lens 112.

As described above, the optical path of the retinal OCT optical system 92 overlaps with the optical path of the anterior segment OCT optical system 90 from the dichroic mirror 104 to the dichroic mirror 110 through the scanner 106, separates from the optical path of the anterior segment OCT optical system 90 from the dichroic mirror 110 until the light is provided again to the dichroic mirror 110 through the lens 120, and overlaps with the optical path of the anterior segment OCT optical system 90 from the dichroic mirror 110 to the subject eye E through the objective lens 112.

The measurement light reflected on the retina of the subject eye E is inputted to the fiber collimator 114 through the objective lens 112, the dichroic mirror 110, the mirrors 126, 124, 122, the lens 120, the dichroic mirror 110, the scanner 106, the perforated mirror 105, the dichroic mirror 104, and the lenses 118, 116. Then, as shown in FIG. 1, it is inputted again to the optical coupler 64 through the optical coupler 68. The measurement light inputted to the optical coupler 64 is inputted to the interference optical system 80.

The light split in the optical coupler 68 of the measurement optical system 66 is inputted to the calibration optical system 30 as described above. As shown in FIG. 1, the light inputted to the calibration optical system 30 is emitted from the fiber collimator that is not shown, and is provided to the dichroic mirror 34 through the lens 38 and the mirror 39. As described above, the dichroic mirror 34 reflects light with a shorter wavelength than 0.90 μm, so the light that has penetrated through the mirror 39 (having the central wavelength of 0.83 μm) is reflected on the dichroic mirror 34. The light reflected on the dichroic mirror 34 is inputted to the calibration mirror 36 through the lens 35. Calibration light reflected on the calibration mirror 36 is inputted again to the fiber collimator through the lens 35, the dichroic mirror 34, the mirror 39, and the lens 38, and then is inputted to the interference optical system 80 through the optical couplers 68, 64.

The reference light split in the optical coupler 64 is inputted to the reference optical system 70 as described above. The reference optical system 70 is provided with lenses 72, 74 and a reference mirror 76. The reference light inputted from the retina light source 62 to the reference optical system 70 is emitted from a fiber collimator that is not shown, and is inputted to the reference mirror 76 through the lenses 72, 74. An optical path length of the reference light outputted from the retina light source 62 is adjusted by a zero-point adjusting mechanism (not shown). The reference light reflected on the reference mirror 76 is inputted again to the fiber collimator and is inputted to the interference optical system 80 through the optical coupler 64.

The interference optical system 80 is provided with lenses 82, 88, a diffraction grating 84, a prism 86, and a light receiving element 89. The measurement light reflected on the subject eye E and the reference light generated by the reference optical system 70 are combined in the interference optical system 80, and the combined measurement interference light is inputted to the light receiving element 89. Further, the calibration light generated by the calibration optical system 30 and the reference light generated by the reference optical system 70 are combined, and the combined calibration interference light is inputted to the light receiving element 89. Specifically, the measurement interference light and the calibration interference light are emitted from a fiber collimator that is not shown, and pass through the lens 82 and the diffraction grating 84. Due to this, each of the interference light is separated into wavelength spectrums. Then, each of the separated light is inputted to the prism 86, by which it is converted from spectrum data that is linear to wavelengths into spectrum data linear to the wave numbers (wavenumber spectrum). Then, each of the light that has been converted into wavenumber spectrum in the prism 86 is inputted to the light receiving element 89 through the lens 88. A line sensor (such as a CCD camera) may be used as the light receiving element, for example. In the light receiving element 89, interference of the measurement interference light and the calibration interference light is measured for each wave number. Then, an interference signal corresponding to an intensity of the measured interference light is inputted to the processor 200 to be described later. The processor 200 is configured to execute Fourier transform processing and the like on the interference signal, by which tomographic images of the retina along scan lines are acquired.

Figure 4:
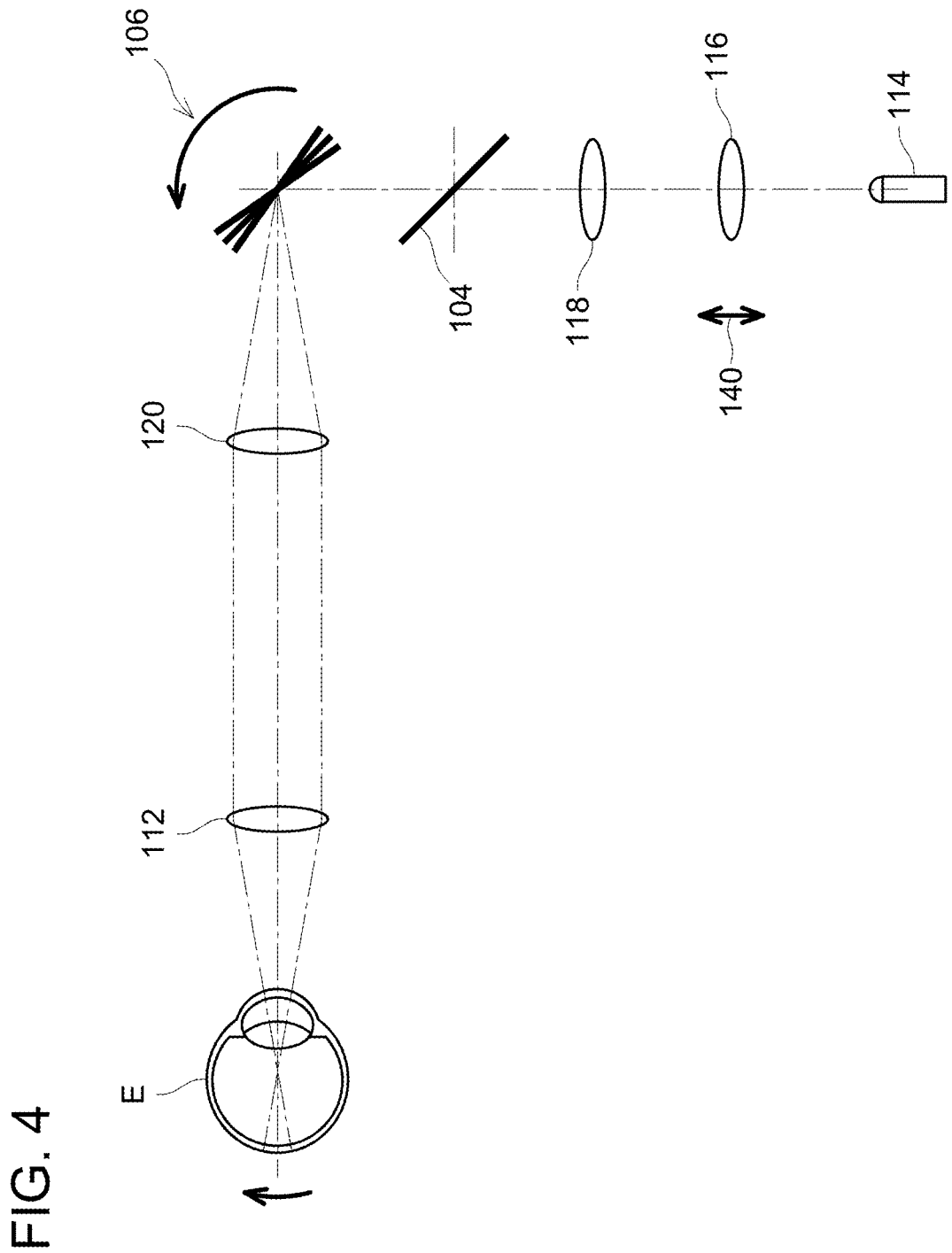
FIG. 4 is a diagram schematically showing an optical path of light in a retinal OCT optical system.

Scan in the retinal OCT optical system 92 will be described with reference to FIG. 4. FIG. 4 shows the optical path along which the light outputted from the fiber collimator 114 reaches the subject eye E. FIG. 4 shows only some of optical members disposed on the optical path (that is, the lenses 116, 118, 120, the dichroic mirror 104, the scanner 106, and the objective lens 112) and omits the other optical members. As shown in FIG. 4, in the retinal OCT optical system 92, the two lenses 112, 120 are disposed between the scanner 106 and the subject eye E. Further, the scanner 106 is disposed at a position conjugate with an intraocular part of the subject eye E. Due to this, pivot scan that forms a pivot inside the subject eye E is executed in the retinal OCT optical system 92. Generally, in case of the pivot scan, the pivot is formed at the pupil of the subject eye E, so if an opaque portion is present in the crystalline lens of the subject eye E for example, it is difficult to sufficiently provide the light to the retina. In this embodiment, the pivot is formed between the retina and the crystalline lens of the subject eye E, therefore the light can easily be provided to the retina regardless of a state of the crystalline lens of the subject eye E.

Further, an end surface of the fiber collimator 114 is disposed at a position conjugate with the retina of the subject eye E. Due to this, the light emitted from the fiber collimator 114 can be concentrated at the retina of the subject eye E. A position of the lens 116 can be changed by actuating a focal point adjusting mechanism 140 to be described later. Due to this, the light emitted from the fiber collimator 114 can be concentrated at the retina of the subject eye E according to the refractive power of the subject eye E. Thus, tomographic images of the retina of the subject eye E can suitably be captured by the retinal OCT optical system 92.

Next, the refraction measurement optical system 94 will be described. The refraction measurement optical system 94 is an optical system used for measuring the refractive power of the subject eye E. In this embodiment, the retina light source 62, which is used in the retinal OCT optical system 92, is used for measuring the refractive power of the subject eye E. The refraction measurement optical system 94 is provided with the fiber collimator 114, lenses 116, 118, 120, 130, 134, the dichroic mirrors 104, 110, the perforated mirror 105, the scanner 106, mirrors 122, 124, 126, 128, the objective lens 112, an aperture 132, a ring lens 136, a sensor 138, the focal point adjusting mechanism 140, and a fogging mechanism (not shown).

In the refraction measurement optical system 94, the light outputted from the retina light source 62 shown in FIG. 1 travels on the same optical path as that of the above-described retinal OCT optical system 92, from the fiber collimator 114 to the subject eye E. That is, in the refraction measurement optical system 94, the light emitted from the fiber collimator 114 is provided to the subject eye E through the lenses 116, 118, the dichroic mirror 104, the perforated mirror 105, the scanner 106, the dichroic mirror 110, the lens 120, the mirrors 122, 124, 126, the dichroic mirror 110, and the objective lens 112.

Reflected light from the subject eye E is provided to the perforated mirror 105 through the objective lens 112, the dichroic mirror 110, the mirrors 126, 124, 122, the lens 120, the dichroic mirror 110, and the scanner 106. The light provided to the perforated mirror 105 is reflected on a reflection surface disposed around the circular hole of the perforated mirror 105, and then is further reflected on the mirror 128. The light reflected on the mirror 128 passes through the lens 130, the aperture 132, the lens 134, and the ring lens 136, and then is detected by the sensor 138. The ring lens 136 includes a ring-shaped lens portion disposed on a lens 134 side and a light shielding portion disposed on a sensor 138 side. The light shielding portion is shielded from light at its portion other than a portion connecting to the lens portion. The light inputted to the ring lens 136 is outputted from the ring lens 136 in form of ring-shaped light. The sensor 138 detects the ring-shaped light outputted from the ring lens 136. The sensor 138 is, for example, a CCD camera, and an image detected (captured) by the sensor 138 is inputted to the processor.

The optical path in the refraction measurement optical system 94 overlaps with the optical path of the retinal OCT optical system 92, from the fiber collimator 114 to the subject eye E. Due to this, the pivot scan is executed in the refraction measurement optical system 94, similarly to the retinal OCT optical system 92. Due to this, similarly to the retinal OCT optical system 92, the refraction measurement optical system 94 can provide the light to the retina regardless of the state of the crystalline lens of the subject eye E. Further, by scanning on the retina, a good image can be acquired even when factors that attenuate the reflection from the retina, such as retinal disorders and blood vessels, are present.

Further, the refraction measurement optical system 94 includes the focal point adjusting mechanism 140. The focal point adjusting mechanism 140 includes an actuating device (not shown) configured to integrally move the fiber collimator 114, the lenses 116, 134, the aperture 132, the ring lens 136, and the sensor 138 in an optical axis direction (Z-axis direction). The focal point adjusting mechanism 140 can integrally move a position of the fiber collimator 114 and a position of the sensor 138 in the optical axis direction by actuating the actuating device. Due to this, the position of the fiber collimator 114 and the position of the sensor 138 can be moved to a position conjugate with the position of the subject eye E according to the refractive power of the subject eye E, by which refractive power measurement can be executed with high accuracy.

Further, the ophthalmic apparatus 1 of the present embodiment disposes the scanner 106 on the overlapping optical path where the optical path of the anterior segment OCT optical system 90 and the optical path of the retinal OCT optical system 92 overlap. That is, the scan in the anterior segment OCT optical system 90 and the scan in the retinal OCT optical system 92 are both executed by the scanner 106. This enables the configuration in the ophthalmic apparatus 1 to avoid becoming complicated and a number of components to be reduced.

Figure 5:
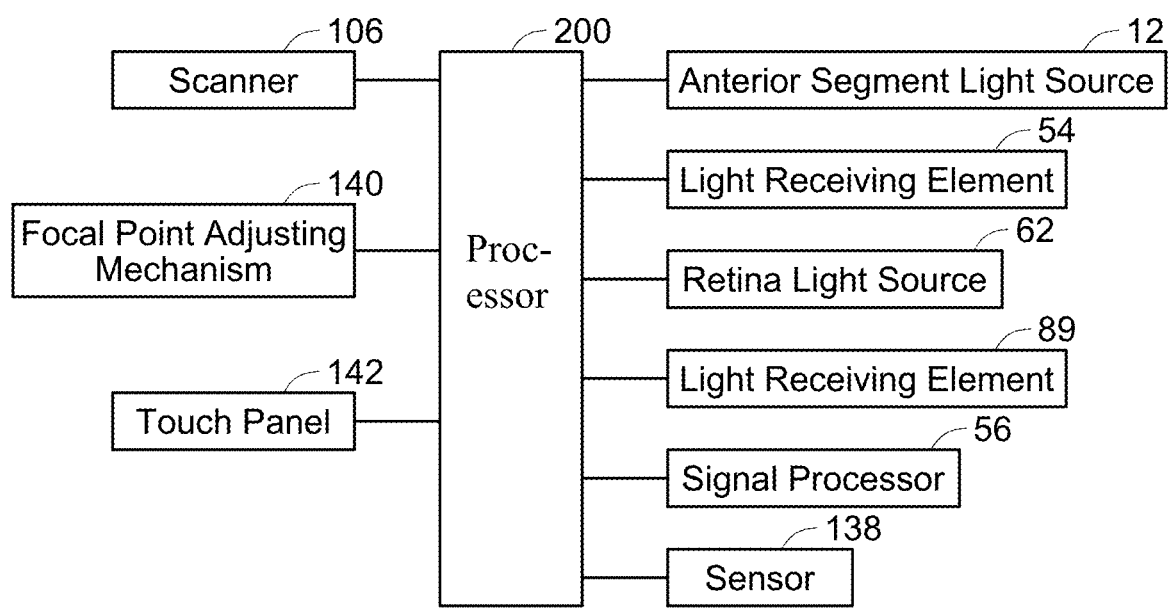
FIG. 5 is a diagram showing a control system of the ophthalmic apparatus of the first embodiment.

A configuration of a control system of the ophthalmic apparatus 1 of the present embodiment will be described with reference to FIG. 5. As shown in FIG. 5, the ophthalmic apparatus 1 is controlled by the processor 200. The processor 200 is configured of a microcomputer (microprocessor) constituted of a CPU, a ROM, a RAM, and the like. The processor 200 is connected to the anterior segment light source 12, the light receiving element 54, and the signal processor 56 in the anterior segment OCT interferometer 10; the retina light source 62 and the light receiving element 89 in the retinal OCT interferometer 11; the scanner 106; the sensor 138; the focal point adjusting mechanism 140; and a touch panel 142.

The processor 200 is configured to scan the light to be provided to the anterior segment of the subject eye E by controlling on/off of the anterior segment light source 12 and driving the scanner 106. Further, the interference signal sampled by the signal processor 56 is inputted to the processor 200. The processor 200 is configured to generate tomographic images by executing Fourier transform on the interference signal, identify positions of the respective parts of the anterior segment of the subject eye E (such as the cornea, anterior chamber, and crystalline lens), and calculate shapes of the respective tissues of the anterior segment.

Similarly, the processor 200 is also configured to scan the light to be provided to the retina of the subject eye E by controlling on/off of the retina light source 62 and driving the scanner 106. Further, the interference signal corresponding to intensity of the interference light detected in the light receiving element 89 is inputted to the processor 200. The processor 200 is configured to generate tomographic images by executing Fourier transform on the interference signal from the light receiving element 89, identify positions of the respective parts of the retina of the subject eye E (such as the retina and choroid), and calculate shapes of the respective tissues of the retina.

Further, electric signals detected by the sensor 138 (captured images) are inputted to the processor 200. The processor 200 is configured to calculate the refractive power of the subject eye E based on the inputted images. The data inputted to the processor 200 and calculation results therefrom are stored in a memory (not shown). Further, the processor 200 is configured to calculate an eye axial length of the subject eye E based on the calculated shapes of the anterior segment and shapes of the retina. Calculation of the eye axial length will be described later.

Further, the processor 200 is configured to control the touch panel 142. The touch panel 142 functions as a display unit that provides various types of information related to the measurement results of the subject eye E to an examiner, and also functions as an input unit that accepts instructions from the examiner. For example, the touch panel 142 can display tomographic images of the anterior segment and the retina of the subject eye E that are generated by the processor 200, a calculated refractive power, and other data acquired by scans. Further, for example, various settings of the ophthalmic apparatus 1 can be inputted to the touch panel 142. The ophthalmic apparatus 1 of the present embodiment is provided with the touch panel 142, however, it simply needs to have a configuration that enables display and input of the aforementioned information, and may have a configuration including a monitor and an input device (such as a mouse and a keyboard).

In the present embodiment, the processor 200 causes the anterior segment light source 12 to output the light to the anterior segment of the subject eye E and causes the retina light source 62 to output the light to the retina of the subject eye E simultaneously, as described above. That is, the processor 200 acquires the interference signal acquired from the anterior segment and the interference signal acquired from the retina by driving the scanner 106 while both the light from the anterior segment light source 12 and the light from the retina light source 62 are inputted to the scanner 106. Due to this, in the present embodiment, the anterior segment and the retina of the subject eye E can be measured while the subject eye E is in substantially the same state. Hereinbelow, processes of measuring the anterior segment, the retina, the refractive power, and the eye axial length of the subject eye E will be described with reference to FIGS. 6 to 15.

Figure 6:
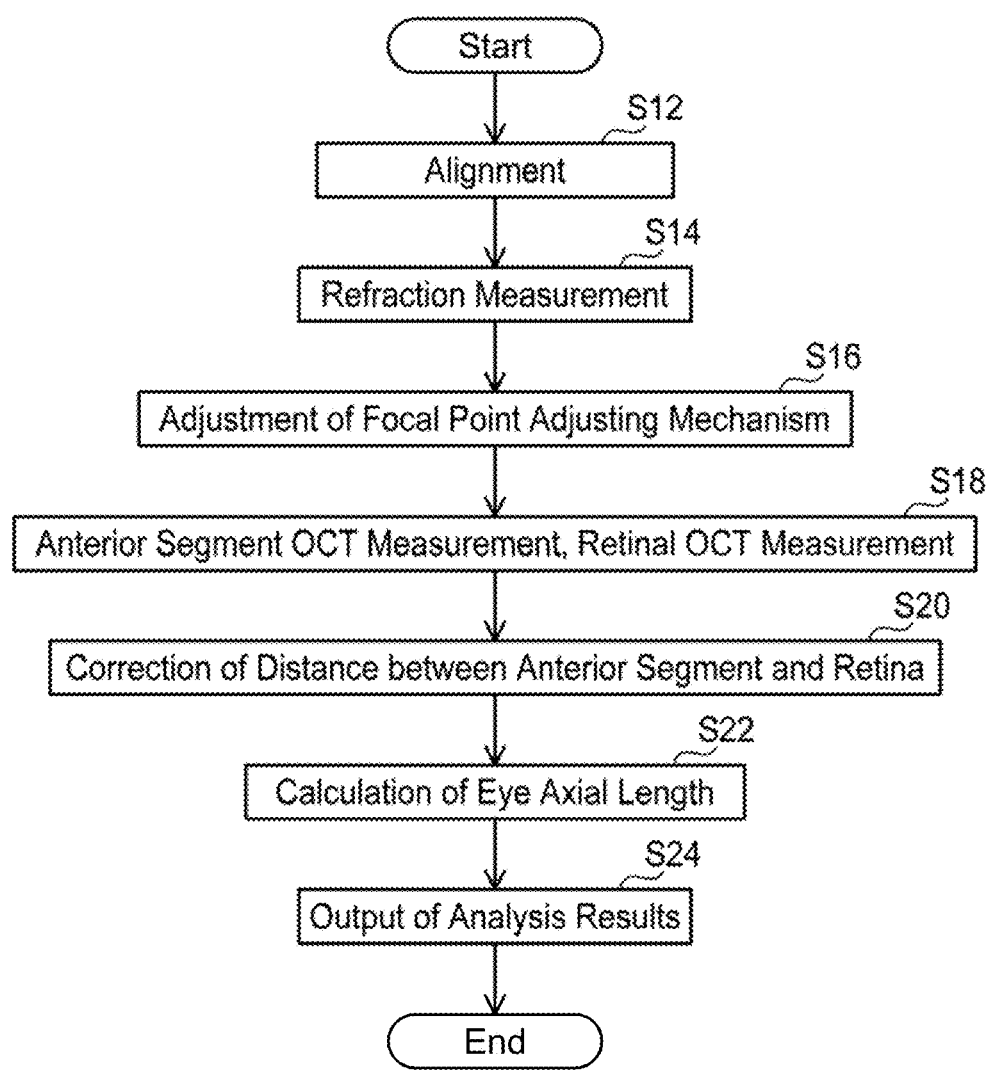
FIG. 6 is a flowchart indicating a process of executing an examination on a subject eye using the ophthalmic apparatus of the first embodiment.

FIG. 6 is a flowchart showing an example of the process of executing the measurements on the subject eye E using the ophthalmic apparatus 1. Firstly, as shown in FIG. 6, when the examiner inputs an examination start instruction to the touch panel 142, the processor 200 aligns the ophthalmic apparatus 1 with respect to the subject eye E (S12). This alignment is executed using the alignment optical system (not shown) provided in the ophthalmic apparatus 1. Methods used in well-known ophthalmic apparatuses can be used for the alignment using the alignment optical system, thus detailed description thereof is omitted.

When the alignment of the ophthalmic apparatus 1 to the subject eye E is completed, the processor 200 executes a refraction measurement (S14). The refraction measurement is executed according to the following procedure. Firstly, the processor 200 adjusts the scanner 106. In doing so, the processor 200 adjusts a circle diameter for scan and an irradiation position on the subject eye E based on a preset value (initial setting value). The initial setting value may be set based on a pupil diameter of an eye sample, for example, to a value smaller than the pupil diameter. Alternatively, if the subject has taken the examination before, the processor 200 may adjust the scanner 106 based on measurement results acquired in the previous examination.

When the adjustment of the scanner 106 is completed, the processor 200 turns on the retina light source 62, takes in the images detected by the sensor 138, and measures the refractive power by analyzing these images. At this occasion, the refractive power may be measured under a state where refractive power adjustment of the crystalline lens of the subject eye E is eliminated by the fogging mechanism (not shown). Since those used in well-known ophthalmic apparatuses can be used as the fogging mechanism, detailed description thereof is omitted.

When the refraction measurement is completed, the processor 200 adjusts the focal point adjusting mechanism 140 based on the results of the refraction measurement of S14 (S16). In a case where the subject eye E is a hypermetropia or myopia, for example, the processor 200 drives the focal point adjusting mechanism 140 to move the positions of the retina light source 62 and the sensor 138 relative to the subject eye E, such that the sensor 138 is located at a position conjugate with the retina of the subject eye E.

Figure 7:
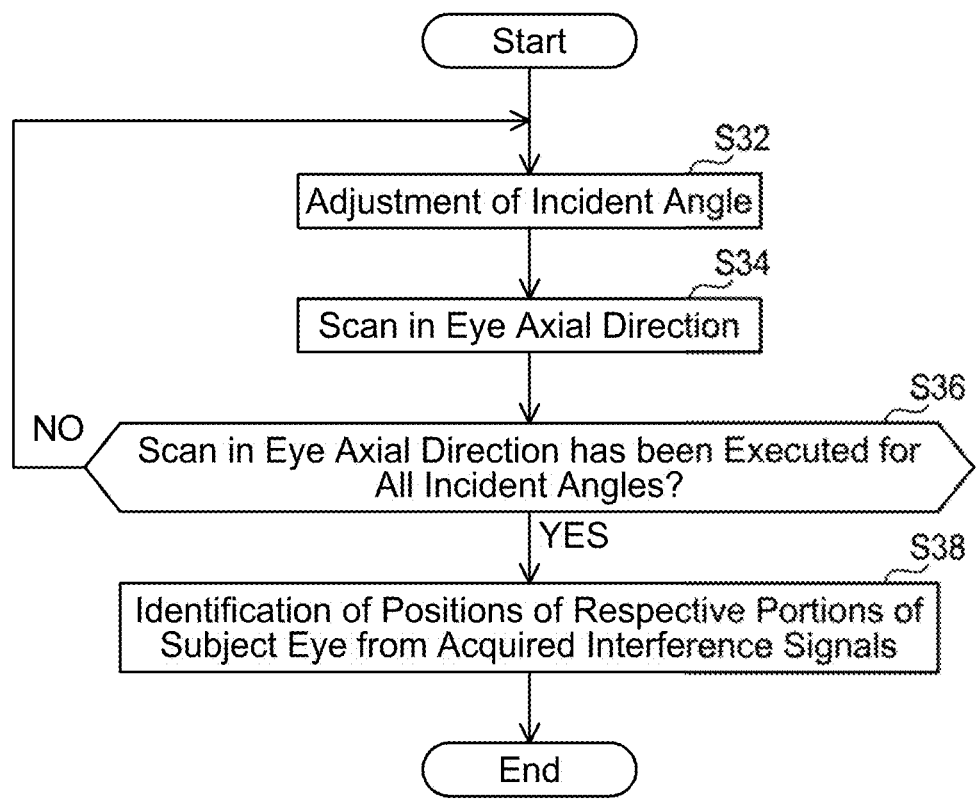
FIG. 7 is a flowchart indicating a process of OCT measurements.

Next, the processor 200 simultaneously executes the anterior segment OCT measurement and the retinal OCT measurement (S18). Firstly, the anterior segment OCT measurement will be described with reference to FIG. 7. As shown in FIG. 7, the processor 200 adjusts the Galvano mirror 108 to one scan angle within a scan angle range (S32). Due to this, the light from the anterior segment light source 12 enters the subject eye E at an incident position and an incident angle that correspond to the adjusted scan angle.

Figure 8:
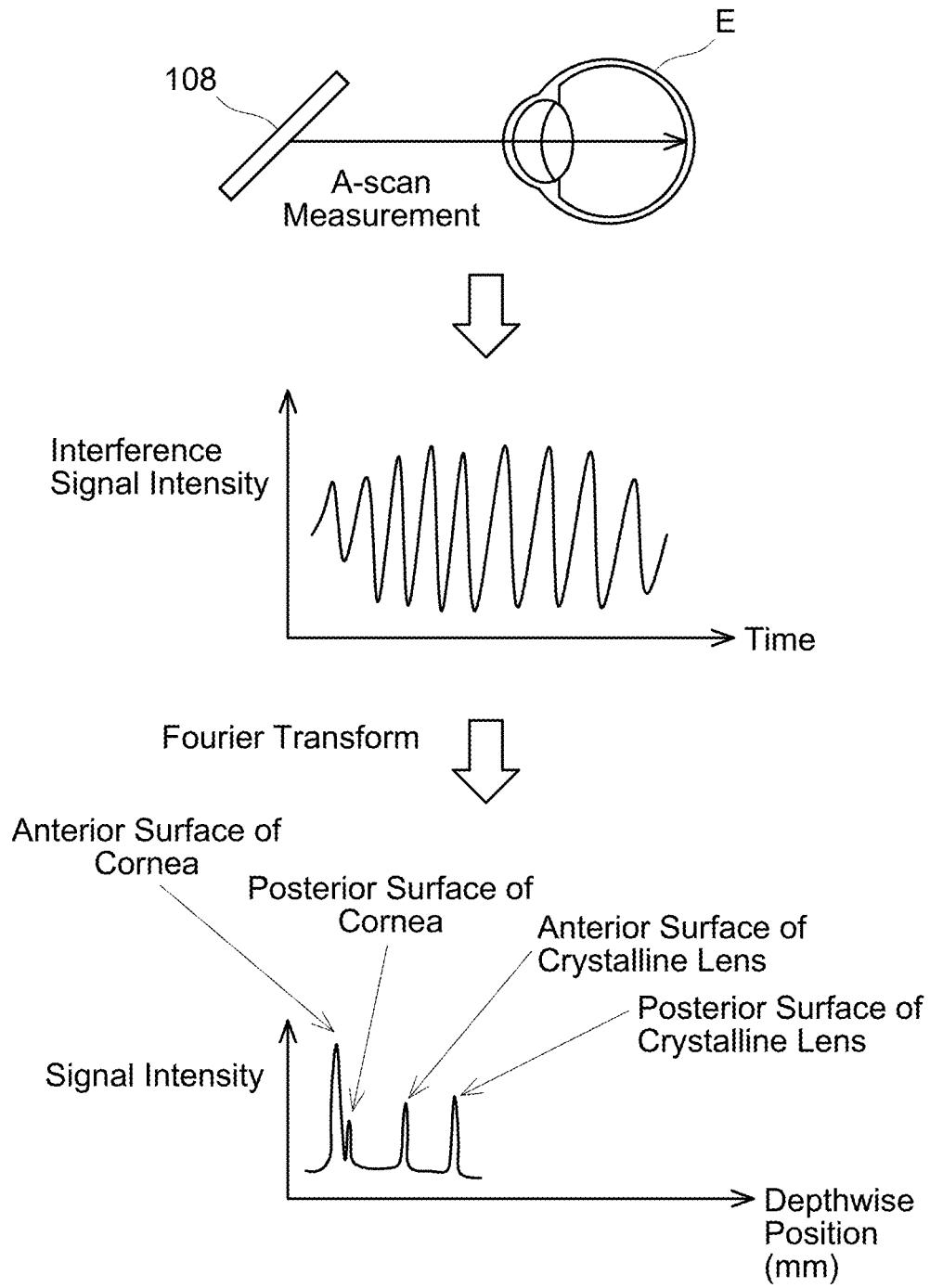
FIG. 8 is a diagram for explaining a procedure of processing an interference signal waveform obtained by the anterior segment OCT interferometer.

When the adjustment of the Galvano mirror 108 is completed, the processor 200 turns on the anterior segment light source 12 and takes in the interference signal sampled by the signal processor 56 while changing the frequency of the light outputted from the anterior segment light source 12 (S34). As shown in FIG. 8, the interference signal sampled by the signal processor 56 becomes a signal of which signal intensity changes over time, and the signal is a signal of interference waves that are resulted from combining the reference light and the respective reflected light reflected on respective parts of the subject eye E (such as anterior and posterior surfaces of the cornea, and anterior and posterior surfaces of the crystalline lens). The processor 200 executes Fourier transform on the signals inputted from the signal processor 56 to identify the positions of the respective parts of the subject eye E in the depth direction from the signals. In the above-described anterior segment OCT measurement, the A-scan speed is set, for example, to about 100 kHz.

Next, the processor 200 determines whether or not the measurement of step S34 has been executed for all of scan angles that were set in advance prior to the measurement (that is, for all of the incident positions and the incident angles) (S36). In a case where the measurement of step S34 has not been executed for all the scan angles yet (NO in step S36), the processor 200 returns to step S32 and repeats the processes of steps S32 to S36. Due to this, interference signal obtained by the A-scan is acquired for the respective scan angles for scanning the Galvano mirror 108. In this embodiment, the Galvano mirror 108 is scanned according to the A-scan speed of the anterior segment OCT measurement (about 100 kHz). In the disclosure herein, changing an incident position and incident angle of light from a light source by changing the scan angle of the Galvano mirror 108 is termed "B-scan". In the anterior segment OCT measurement, the Galvano mirror 108 is scanned so that a B-scan range (B-scan width) becomes about 16 mm, for example.

Figure 9:
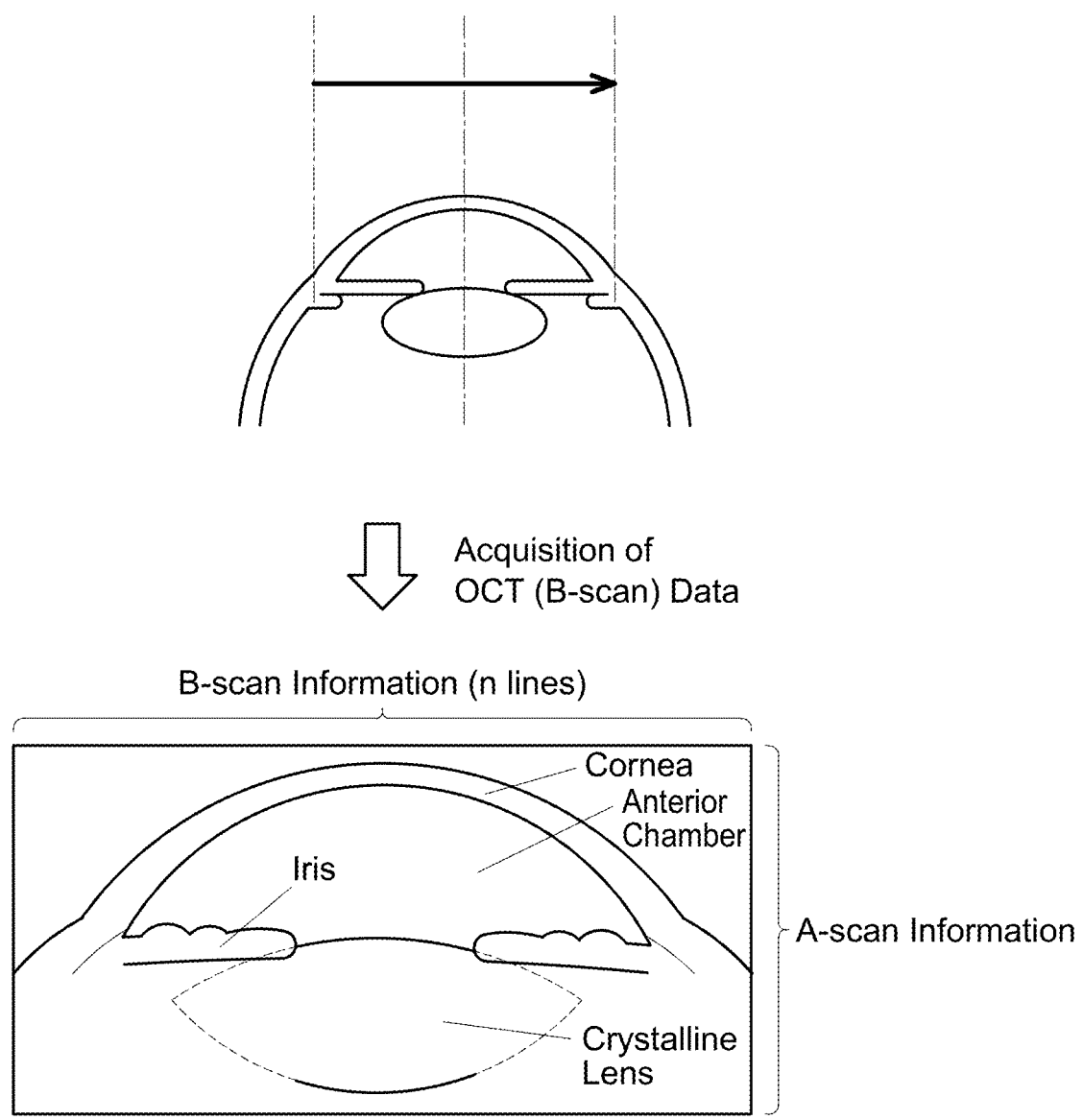
FIG. 9 is a diagram for explaining a procedure of scanning incident positions of light to the subject eye within a predetermined range and identifying positions of respective parts of the subject eye from information obtained for the respective incident positions (information obtained by the procedure shown in FIG. 8).

In a case where the measurement of step S34 has been executed for all the scan angles (YES in step S36), the processor 200 identifies the positions of the respective portions of the subject eye E (such as the anterior and posterior surfaces of the cornea, the anterior and posterior surfaces of the crystalline lens) from the interference signal acquired for the respective scan angles (S38). Specifically, when the process of step S34 is executed for each of the scan angles, interference signal information (A-scan information) is acquired for each of the scan angles. Accordingly, as shown in FIG. 9, two-dimensional information in which the interference signal information (A-scan information), which are as many as the number of the scan angles (n lines), are arranged is acquired. Due to this, the processor 200 identifies the positions of the respective portions of the subject eye E by calculating borderlines between the portions of the subject eye E (such as the cornea, the anterior chamber, an iris, and the crystalline lens) included in the interference signal information. In the anterior segment OCT measurement, the A-scan information are acquired for about 800 scan angles, for example. As such, two-dimensional information in which about 800 pieces of interference signal information (A-scan information) are arranged is acquired.

Figure 10A:
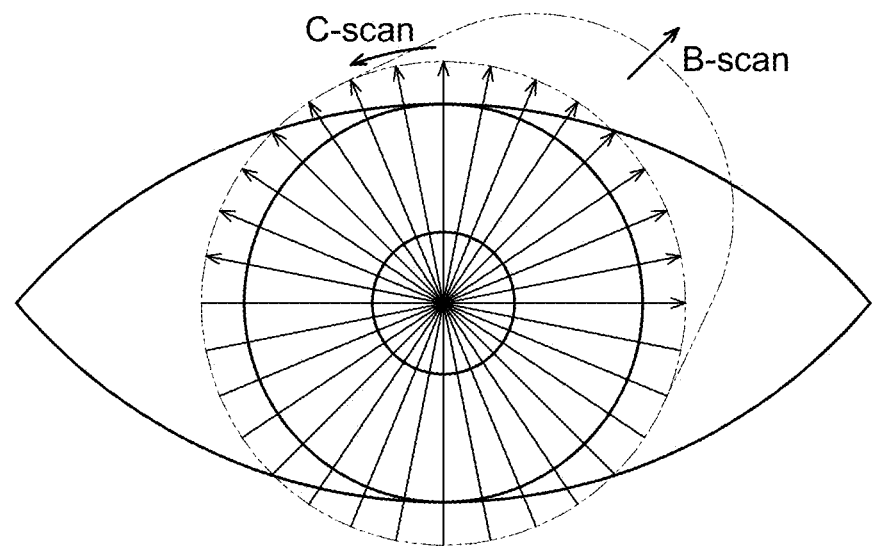
FIGS. 10A and 10B are diagrams for explaining a radial scan scheme in an anterior segment OCT measurement.
Figure 10B:
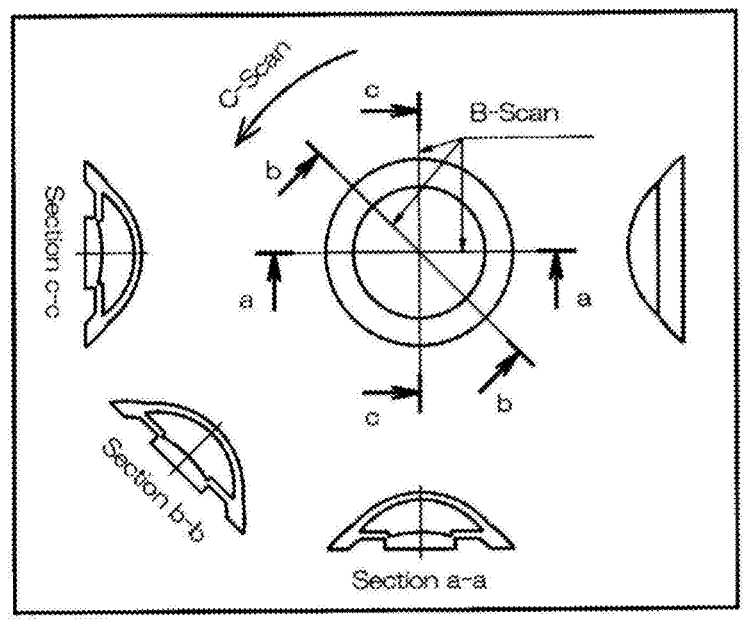

In this embodiment, the anterior segment OCT measurement in step S18 is executed by a radial scan scheme shown in FIGS. 10A, B. Due to this, tomographic images of the anterior segment are obtained over an entire region. That is, B-scan directions are set radially from an apex of the cornea of the subject eye E, and tomographic images are acquired with a C-scan direction set as a circumferential direction. The processor 200 takes in data of the acquired (captured) tomographic images in the memory.

As described above, the anterior segment OCT optical system 90 executes the telecentric scan. Due to this, tomographic images without distortion can be acquired in the anterior segment OCT measurement. Further, in the anterior segment OCT optical system 90, the end surface of the fiber collimator 102 is located at the position conjugate with the position of the anterior segment of the subject eye E, and the anterior segment light source 12 outputs the light with the suitable wavelength for capturing the tomographic images of the anterior segment of the subject eye E. Due to this, the shapes of the anterior segment of the subject eye E can suitably be calculated in the anterior segment OCT measurement.

Next, the retinal OCT measurement will be described. As described above, the retinal OCT measurement is executed simultaneously with the anterior segment OCT measurement (S18). As such, the retinal OCT measurement is also executed according to the flowchart shown in FIG. 7, similarly to the anterior segment OCT measurement. Specifically, the processor 200 turns on the retina light source 62 along with the anterior segment light source 12 to cause the light from the retina light source 62 to enter the subject eye E at the incident position and the incident angle corresponding to the scan angle adjusted in step S32 described above, and takes in the interference signal of the light separated in the wavenumber spectrum (S34). The processor 200 outputs the light from the retina light source 62 in pulses and receives the signals from the light receiving element 89 in synchrony with that light output. That is, the processor 200 acquires the interference signal while repeating on and off of the retina light source 62 with a predetermined period. The pulse output of light in the retinal OCT measurement will be described later. In the retinal OCT measurement, the A-scan speed is set, for example, to about 10 kHz.

Figure 11:
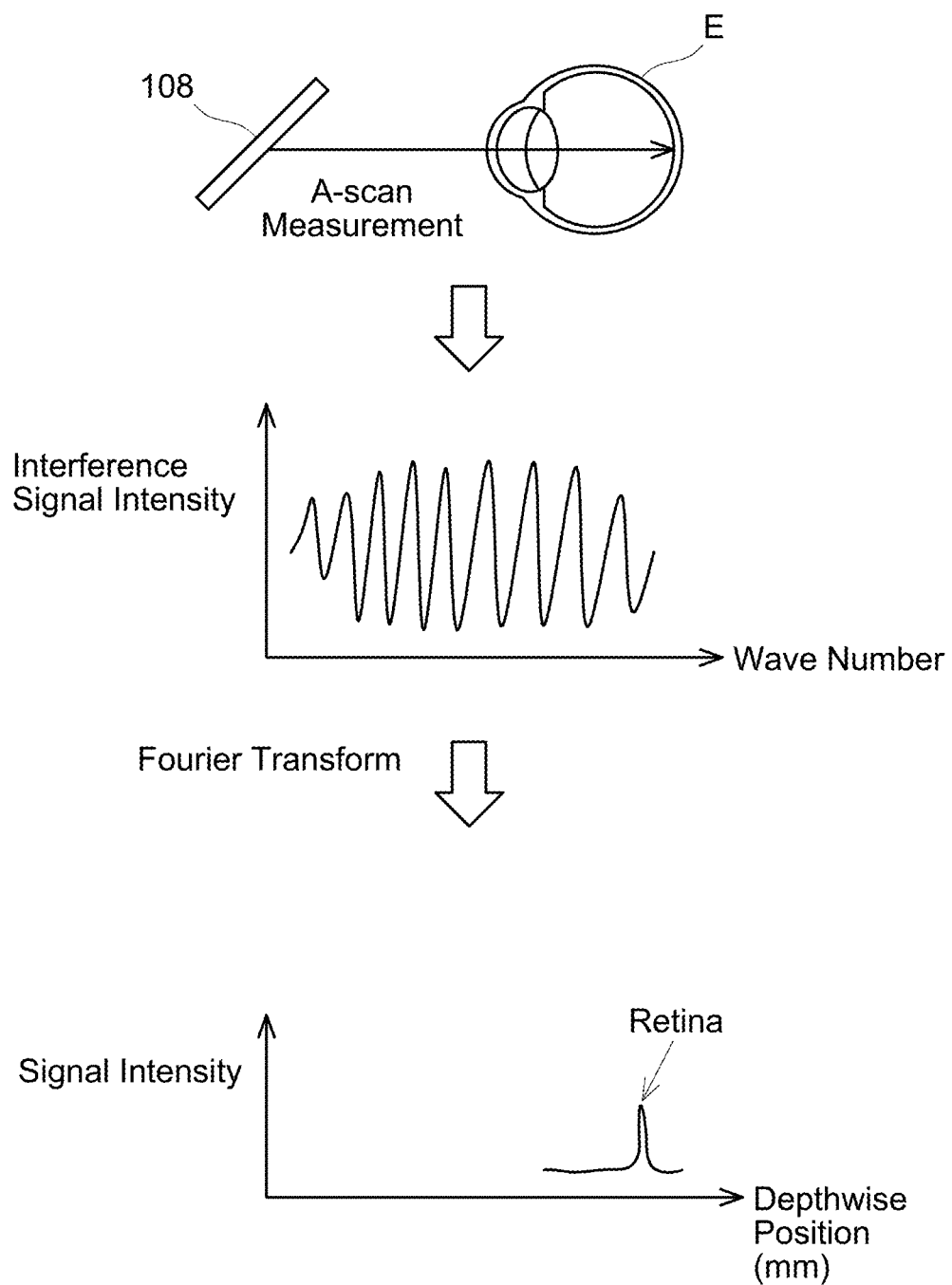
FIG. 11 is a diagram for explaining a procedure of processing an interference signal waveform obtained by the retinal OCT interferometer.

In the retinal OCT optical system 92, the retina light source 62 outputs the light with the wavelength that reaches the retina of the subject eye E, and the respective optical members are disposed so that the light outputted from the retina light source 62 concentrates at the retina of the subject eye E. Due to this, as shown in FIG. 11, the processor 200 can identify the positions of retina portion of the subject eye E such as the retina. This measurement is repeated until it is executed for all the preset scan angles, similarly to step S36. In the retinal OCT measurement, the Galvano mirror 108 is scanned so that the B-scan range becomes, for example, 3.8 mm Further, in the retinal OCT measurement, the A-scan information is obtained for about 80 scan angles, for example. In this embodiment, the light outputted from the retina light source 62 and the light outputted from the anterior segment light source 12 are scanned simultaneously by the scanner 106. Due to this, in the above-described alignment of step S12, the positions of the scanner 106, the objective lens 112, the lens 120 and the like are adjusted based on a focal length of the objective lens 112 and the like so that the B-scan range in the anterior segment OCT measurement and the B-scan range in the retinal OCT measurement have the aforementioned ranges (that is, the range of about 16 mm and the range of about 3.8 mm, respectively).

In this embodiment, the A-scan speed in the retinal OCT measurement (about 10 kHz) is slower than the A-scan speed in the anterior segment OCT measurement (about 100 kHz). Due to this, when the light in these measurements are scanned simultaneously by the scanner 106, the number of the A-scan information (number of A-scans) obtained by the retinal OCT measurement is less than the number of the A-scan information obtained by the anterior segment OCT measurement. Here, generally in an OCT measurement that employs the Fourier domain scheme, a phenomenon where an interference signal acquired from interference light attenuates or vanishes is known to occur when the B-scan executed together with the A-scan (changes in an incident position and an incident angle of measurement light caused by a change in a scan angle of a mirror (that is, scan of the measurement light in a direction orthogonal to a depth direction of a subject eye)) is executed at a relatively high speed, because a scan angle changes while the A-scan measurement is executed at that certain angle and the original measurement position is thereby displaced. That is, in this embodiment, the phenomenon in which the interference signal acquired from the interference light attenuates (a so-called fringe washout) may occur when a scan resolution in the OCT measurement (which is the B-scan range per one A-scan (that is, an interval between adjacent A-scans)) is lower than an optical resolution in the OCT measurement. Therefore, the scan resolution may be set higher than the optical resolution. Hereinbelow, derivation of the scan resolution and the optical resolution will be described.

Figure 12:
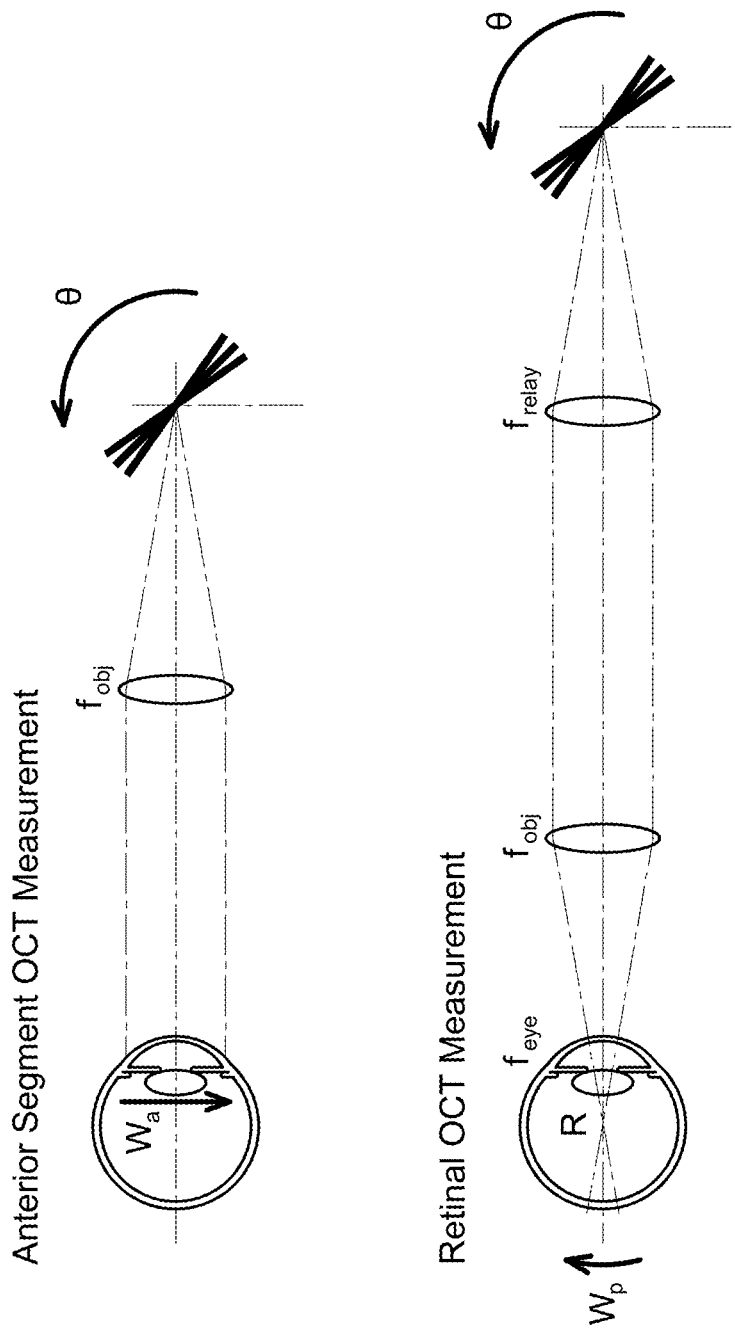
FIG. 12 are diagrams for explaining derivation of a scan resolution in OCT measurements.

FIG. 12 show diagrams for explaining the derivation of the scan resolution in the anterior segment OCT measurement and the retinal OCT measurement. As shown in FIG. 12, assuming that the B-scan range of the anterior segment OCT measurement is Wa, the focal length of the objective lens is $f_{obj}$, and an oscillation angle of the Galvano mirror is θ, a total oscillation angle for beam on a surface of the Galvano mirror is 2θ, thus a relationship of Wa=$f_{obj}$·2 tan θ is established. Further, assuming that a magnification of the Galvano mirror is Ma in a case where the Galvano mirror is not a stereo but a real image, a relationship of Wa=$f_{obj}$·2 tan θ/Ma is established. On the other hand, assuming that the B-scan range of the retinal OCT measurement is Wp, the focal length of the objective lens is $f_{obj}$, the focal length of the lens is $f_{relay}$, an eye focal length of the subject eye is $f_{eye}$, and the oscillation angle of the Galvano mirror is θ, a relationship of Wp=($f_{eye}$·$f_{relay}$/$f_{obj}$)·2 tan θ is established. Further, assuming that a magnification of a real image R relative to the Galvano mirror is Mp, a relationship of Wp=$f_{eye}$·2 tan θ/Mp is established. As such, assuming that the number of A-scans in one B-scan is Np, the scan resolution δWp of the retinal OCT measurement can be represented as δWp=($f_{eye}$·2 tan θ/Mp)/Np.

In this embodiment, the scanner 106 is shared in the anterior segment OCT measurement and in the retinal OCT measurement. Due to this, the oscillation angle θ of the Galvano mirror 108 is mutual in the anterior segment OCT measurement and the retinal OCT measurement. Thus, the scan resolution δWp in the retinal OCT measurement can be represented as δWp=($f_{eye}$/$f_{obj}$)·(Ma/Mp)·(Wa/Np). Further, assuming that a time required for one B-scan is T, the A-scan speed in the anterior segment OCT measurement is Fa and the number of A-scans therein is Na, and the A-scan speed in the retinal OCT measurement is Fp and the number of A-scans therein is Np, a relationship of T=Na/Fa=Np/Fp is established. Thus, in this embodiment, the scan resolution δWp in the retinal OCT measurement is derived as δWP= ($f_{eye}$/$f_{obj}$)·(Ma/Mp)·(Wa/Na)·(Fa/Fp).

Figure 13:
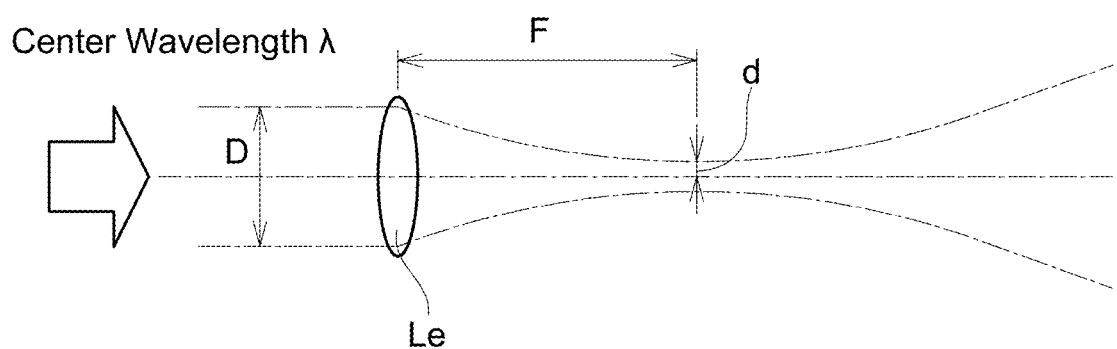
FIG. 13 is a diagram for explaining derivation of an optical resolution in the OCT measurements.

FIG. 13 shows a diagram for explaining the derivation of the scan resolution in the retinal OCT measurement. In a case where the light outputted from the light source is in a single mode, as shown in FIG. 13, the optical resolution 2d is represented as 2d=(4λ/π)·(F/D), where the central wavelength of the light is λ, the focal length of the lens Le is F, and the beam diameter of the light entering the lens Le is D. As such, in the present embodiment, the optical resolution 2dp of the retinal OCT measurement is derived as 2dp= (4λp/π)·($f_{eye}$/Dp), where the central wavelength of the light outputted from the retina light source 62 is λp, the eye focal length of the subject eye E is $f_{eye}$, and the beam diameter of the light entering the cornea is Dp.

As described above, in order to suppress the fringe washout from occurring, the scan resolution needs to be higher than the optical resolution. That is, a relationship of δWp<2dp needs to be established. Thus, in a case where a relationship of (Fp·λp·Mp)/Dp>(π/4)·(Ma/$f_{obj}$)·(Wa/Na)·Fa is established from the scan resolution and the optical resolution of the retinal OCT measurement derived above, the fringe washout can be suppressed from occurring. In the present embodiment, since the conditions of the anterior segment OCT measurement are Fa=100 kHz, Wa=16 mm, and Na=800 lines as described above, the A-scan speed Fp in the retinal OCT measurement is set to Fp>27036 Hz when the other conditions are set, for example, as Ma=1, $f_{obj}$=70 mm, λp=0.83 μm, Dp=1 mm, and Mp=1, by which occurrence of the fringe washout can be suppressed.

In the present embodiment, the A-scan speed of the retinal OCT measurement is set to about 10 kHz. Due to this, if the light is continuously outputted from the retina light source 62, the fringe washout occurs in the interference signal acquired in the retinal OCT measurement. Contrary to this, in the present embodiment, the A-scan speed is set to about 10 kHz in the retinal OCT measurement and the light from the retinal light source 62 is outputted in pulses with a period according to the A-scan speed in the retinal OCT measurement. In case of the present embodiment, the fringe washout can be suitably suppressed from occurring by outputting the light from the retina light source 62 in pulses with a period 1/Fp at a duty cycle that is less than Fp/{n/(4λp)·(Dp/$f_{obj}$)· (Ma/Mp)·(Wa/Na)·Fa}. That is, in the present embodiment, the light is outputted from the retinal light source 62 in pulses with the duty cycle of less than 10000/27036 and with a period of 100 μs, by which the occurrence of the fringe washout is suppressed.

Figure 14:
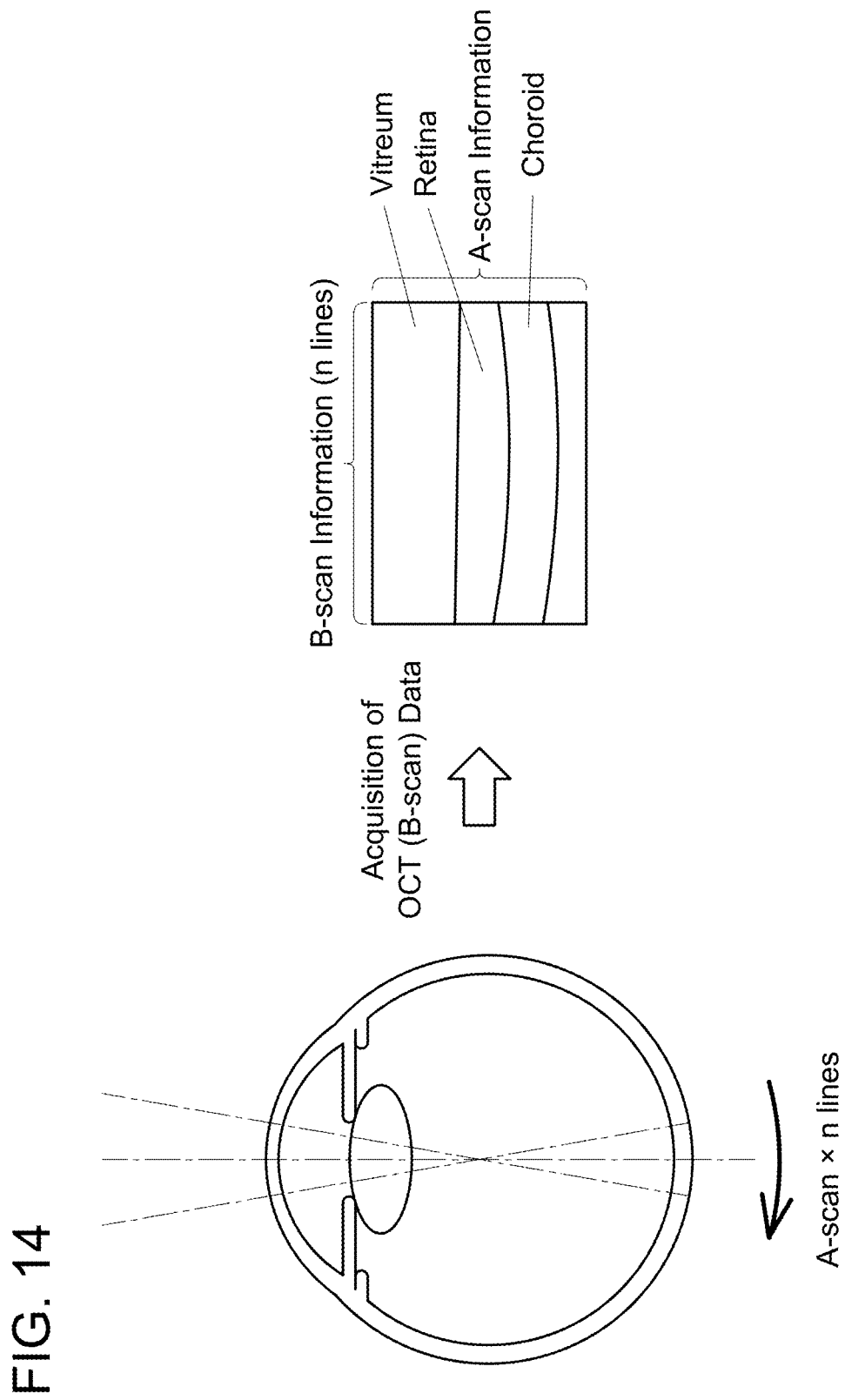
FIG. 14 is a diagram for explaining a procedure of scanning incident positions and incident angles of light to the subject eye within predetermined ranges and identifying positions of the respective parts of the subject eye from information obtained for the respective incident positions and incident angles (information obtained by the procedure shown in FIG. 12).

When the measurement is completed for all the scan angles, the processor 200 identifies the positions of the respective parts of the subject eye E (such as the retina and choroid) from the interference signal obtained for the respective scan angles, similar to S38 described above. Unlike the anterior segment OCT optical system 90, the retinal OCT optical system 92 executes the pivot scan. Due to this, as shown in FIG. 14, two-dimensional information that connects the pivots in the subject eye E in each of the scan angles is acquired. Due to this, the processor 200 identifies the positions of the respective parts of the subject eye E by calculating average values of the position information of the parts of the subject eye E included in the respective interference signal information. The shapes of the retina of the subject eye E can be calculated from these measurement results.

Figure 15:
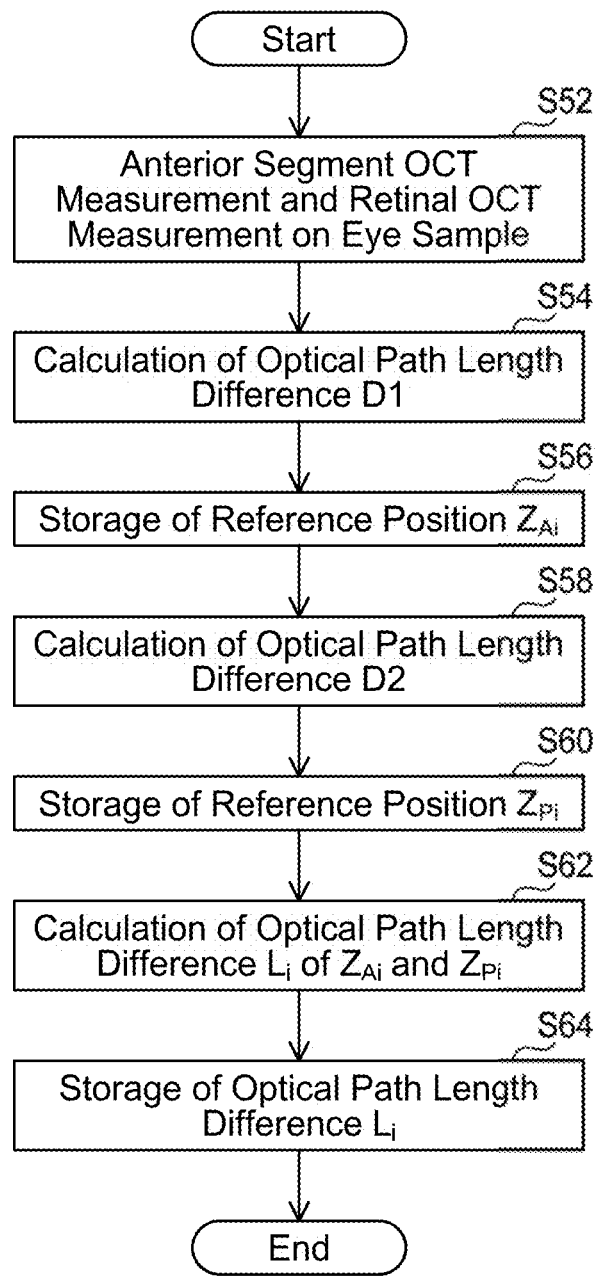
FIG. 15 is a diagram for explaining correction of a distance between an anterior segment and a retina.
Figure 16:
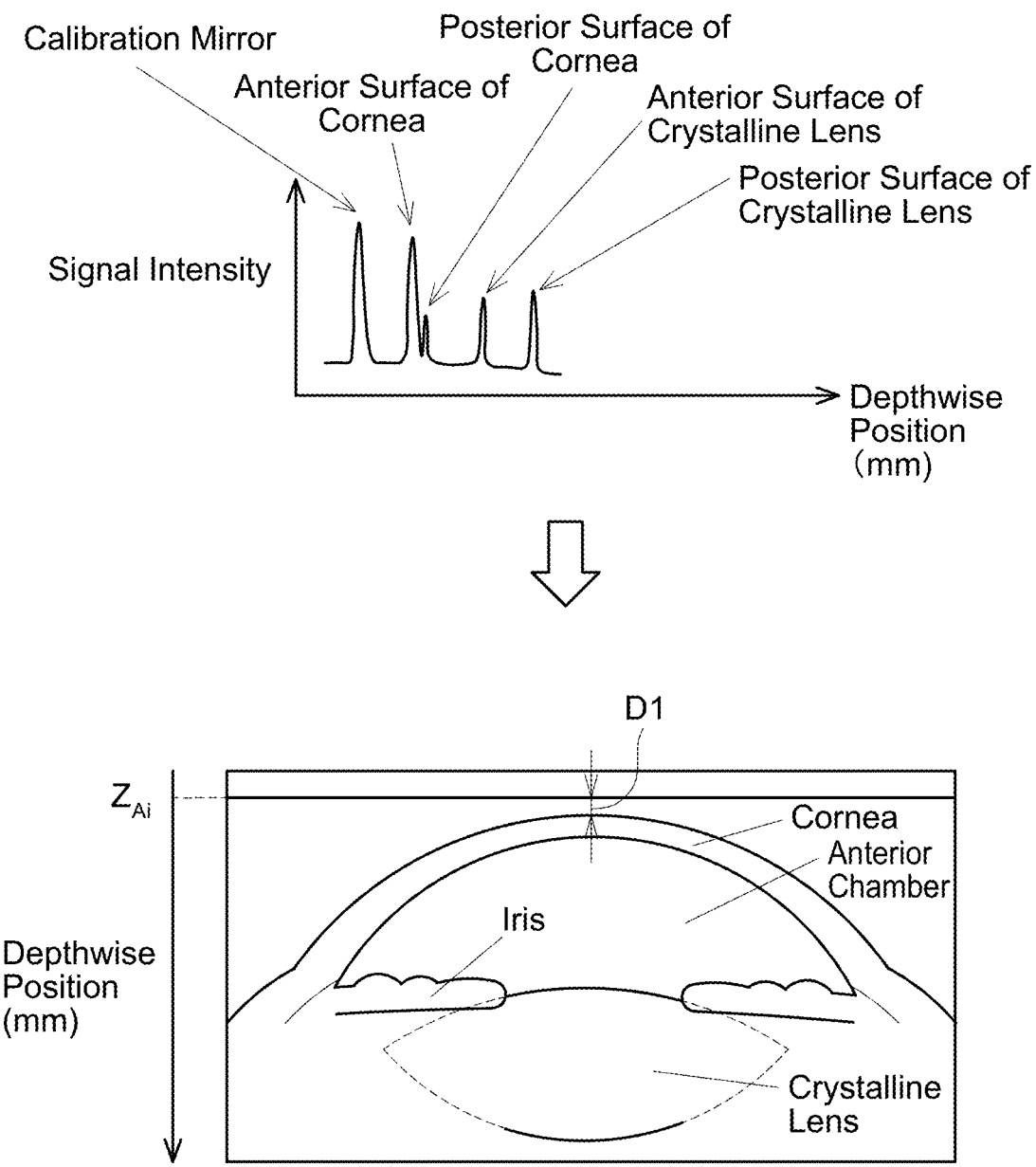
FIG. 16 is a diagram for explaining acquisition of a peak indicating a depth position of a calibration mirror in the anterior segment OCT measurement.

When the calculation of the shapes of the anterior segment and the calculation of the shapes of the retina are completed, the processor 200 corrects a distance between the anterior segment and the retina of the subject eye E based on the interference signal acquired from the calibration mirror 36 (S20). The correction of the distance between the anterior segment and the retina will be described with reference to FIG. 15. A process of FIG. 15 is executed prior to the examination of the subject eye E. As shown in FIG. 15, the processor 200 firstly executes the anterior segment OCT measurement and the retinal OCT measurement on a target object having a known optical path length (for example, an eye sample) (S52). When the anterior segment OCT measurement is executed on the eye sample, as shown in FIG. 16, peaks indicating depth positions of respective parts of an anterior segment of the eye sample that are acquired from the measurement interference light and a peak indicating a depth position of the calibration mirror 36 acquired from the calibration interference light are acquired. By acquiring the peak that indicates the depth position of the calibration mirror 36 for each scan angle, the processor 200 superposes signals that indicate the depth position of the calibration mirror 36 onto the tomographic images of the anterior segment and calculates a difference D1 between an optical path length from the anterior segment light source 12 to a predetermined part of the anterior segment (for example, the anterior surface of the cornea) and an optical path length from the anterior segment light source 12 to the calibration mirror 36 (S54). Further, the processor 200 stores the depth position of the calibration mirror 36 in the interference signal in the anterior segment OCT measurement as a reference position $Z_{Ai}$ (S56).

Figure 17:
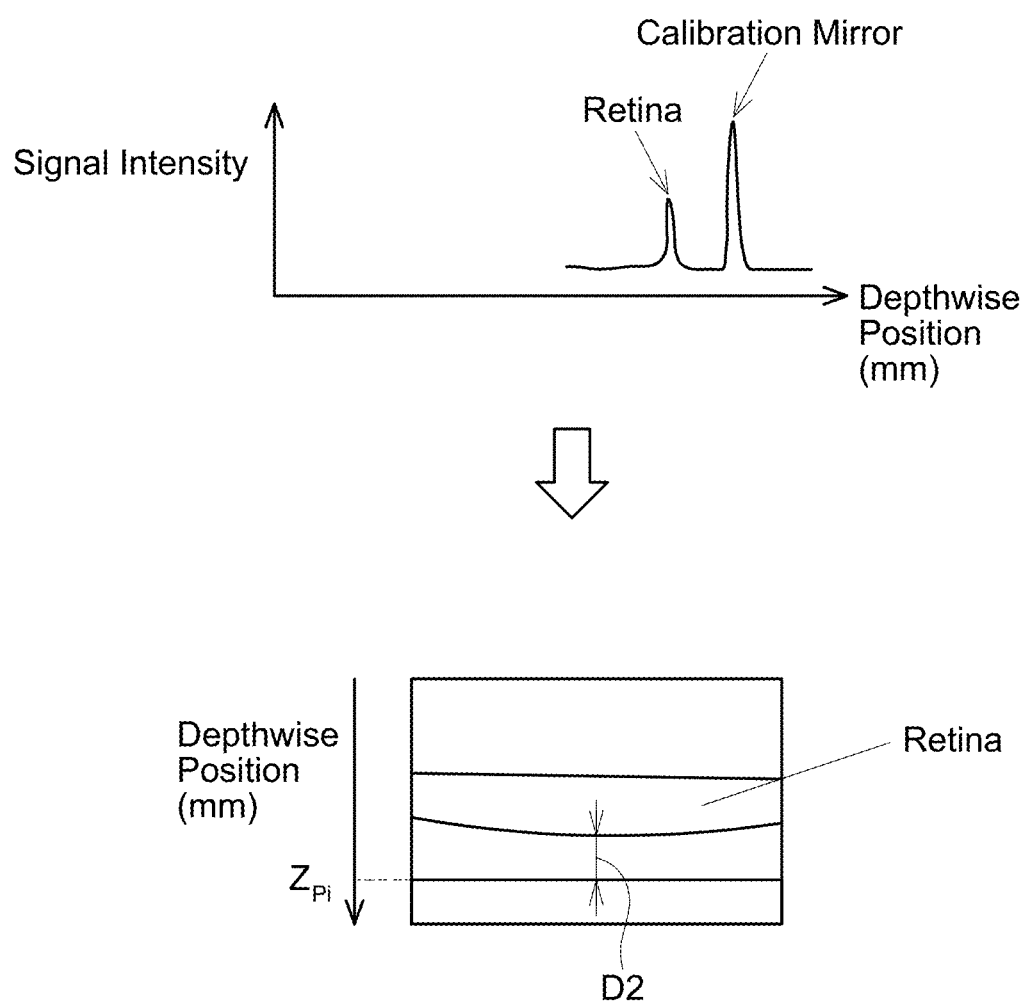
FIG. 17 is a diagram for explaining acquisition of a peak indicating a depth position of the calibration mirror in a retinal OCT measurement.

Similarly, the processor 200 executes the retinal OCT measurement on the eye sample and acquires peaks indicating depth positions of respective parts of a retina of the eye sample acquired from the measurement interference light and a peak indicating the depth position of the calibration mirror 36 acquired from the calibration interference light, as shown in FIG. 17. By acquiring the peak that indicates the depth position of the calibration mirror 36 for each scan angle, the processor 200 superposes signals indicating the depth position of the calibration mirror 36 onto the tomographic images of the retina and calculates a difference D2 between an optical path length from the retina light source 62 to a predetermined part of the retina (for example, the retina) and an optical path length from the retina light source 62 to the calibration mirror 36 (S58). Further, the processor 200 stores the depth position of the calibration mirror 36 in the interference signal in the retinal OCT measurement as a reference position $Z_{Pi}$ (S60).

Then, the processor 200 calculates a distance (optical path length difference) $L_i$ between the reference position $Z_{Ai}$ and the reference position $Z_{Pi}$ (S62). The depth positions of the respective parts of the eye sample are known. Thus, for example, the optical path length difference $L_i$ between the reference position $Z_{Ai}$ and the reference position $Z_{Pi}$ can be calculated based on a distance from the anterior surface of the cornea to the retina of the eye sample and the calculated optical path length differences D1, D2. The processor 200 stores the calculated optical path length difference $L_i$ in the memory (S64).

In the OCT measurements by the ophthalmic apparatus 1, the optical path lengths of the interferometers 10, 11 may change. For example, if the optical path length of the anterior segment OCT interferometer 10 at the time when the subject eye E is to be measured changes from the optical path length of the anterior segment OCT interferometer 10 at the time when the eye sample was measured, the depth position of the calibration mirror 36 in the interference signal at the time when the subject eye E is to be measured is displaced from the reference position $Z_{Ai}$ of the calibration mirror 36 in the interference signal at the time when the eye sample was measured. In the present embodiment, even in such a case where the optical path length of the interferometer has changed, the optical path length differences of the interferometers 10, 11 at the time of the OCT measurements can be calculated based on the reference positions $Z_{Ai}$, $Z_{Pi}$ of the calibration mirror 36. Specifically, assuming that the depth positions of the calibration mirror 36 at the time when the anterior segment OCT measurement and the retinal OCT measurement are executed on the subject eye E in S18 of FIG. 6 are respectively $Z_A$ and $Z_P$, a distance (optical path length difference) L from the depth position $Z_A$ to the depth position $Z_P$ can be calculated as $L=L_i+(Z_A-Z_{Ai})+(Z_P-Z_{Pi})$. As above, the distance from the anterior segment to the retina is corrected by calculating the optical path length difference L at the time of the actual measurements (S20).

When the correction of the distance between the anterior segment and the retina is completed, the processor 200 calculates the eye axial length of the subject eye E (S22). That is, the eye axial length of the subject eye E is calculated based on the depth positions $Z_A$, $Z_P$ and the optical path length difference L calculated in S20, the depth positions of the respective parts of the anterior segment calculated in the anterior segment OCT measurement, and the depth positions of the respective parts of the retina calculated in the retinal OCT measurement.

When all the measurements (the refraction measurement, the anterior segment OCT measurement, and the retinal OCT measurement) are completed, the processor 200 outputs the analysis results to the touch panel 142 (S24). Since the ophthalmic apparatus 1 of the present embodiment can execute plural types of measurements, namely the anterior segment OCT measurement, the retinal OCT measurement, and the refraction measurement, it can comprehensively analyze the state of the subject eye. By executing the measurements on the subject eye E before a cataract surgery, IOL power calculation, cornea aberration, and opaque state of the crystalline lens can be calculated as the analysis results, for example. Further, by executing the measurements on the subject eye before the cataract surgery, errors with respect to postoperative refractive power of the subject eye E that is predicted before the surgery can be evaluated, and this can be used to improve accuracy of the IOL power calculation. Further, by executing the measurements on a subject eye suffering glaucoma, progression of the glaucoma can be predicted from a retina thickness distribution, and a closure angle thereof may be screened. Further, by executing the measurements on an excessively-myopia subject, the state of the subject eye can be examined in detail and comprehensively.

As described above, in the ophthalmic apparatus 1 of the present embodiment, the central wavelength of the light outputted to the anterior segment and the central wavelength of the light outputted to the retina differ from each other. Due to this, the examinations of the anterior segment and the retina can be executed by outputting the light with the wavelengths suitable for the examinations of the anterior segment and the retina. Thus, according to the ophthalmic apparatus 1 of this embodiment, the measurements of the anterior segment and the retina can accurately be executed. Further, in the ophthalmic apparatus 1 of the present embodiment, the optical path of the light outputted from the anterior segment light source 12 and the optical path of the light outputted from the retina light source 62 partially overlap with each other. Due to this, the subject eye E can be irradiated with both of the light simultaneously. Thus, according to the ophthalmic apparatus 1 of this embodiment, the examinations on different ranges of the subject eye E (that is, the anterior segment and the retina) can efficiently be executed. Due to this, the plural types of measurements on the subject eye E can be executed on the subject eye E that is in the substantially same state. As above, the ophthalmic apparatus 1 can reduce burden on the subject and execute the plural types of measurements on the subject eye E accurately.

Further, in the ophthalmic apparatus 1 of the present embodiment, the scanner 106 is used for all of the plural types of measurements (the anterior segment OCT measurement, the retinal OCT measurement, and the refraction measurement). Due to this, the configurations of the optical systems in the ophthalmic apparatus 1 can be suppressed from becoming complicated, and the number of components can be reduced.

Further, in the ophthalmic apparatus 1 of the present embodiment, the light source used in the refraction measurement is used as the light source used in the retinal OCT measurement (the retina light source 62). This enables the configuration of the ophthalmic apparatus 1 to avoid becoming complicated and the number of components to be reduced.

Further, in the ophthalmic apparatus 1 of the present embodiment, the scanner 106 is shared between the anterior segment OCT measurement and the retinal OCT measurement, and the A-scan speed in the retinal OCT measurement (about 10 kHz) is set slower than the A-scan speed in the anterior segment OCT measurement (about 100 kHz). Due to this, if the retina light source 62 outputs the light continuously, the fringe washout easily occurs in the retinal OCT measurement when the scanner 106 is scanned according to the A-scan speed in the anterior segment OCT measurement. However, in the present embodiment, the light is outputted from the retina light source 62 in pulses with the predetermined period. This makes the scan resolution in the retinal OCT measurement higher than the optical resolution thereof, thus the fringe washout in the retinal OCT measurement can be suitably suppressed.

Further, in the ophthalmic apparatus 1 of the present embodiment, the distance between the anterior segment and the retina is corrected using the calibration mirror 36. In the present embodiment, in the examinations of the anterior segment and the retina, the two interferometers, namely the anterior segment OCT interferometer 10 and the retinal OCT interferometer 11, are used. Due to this, as compared to a case where only one interferometer is used, the difference between the optical path lengths of the interferometers 10, 11 changes relatively easily, and an error tends to be caused in calculating the distance between the anterior segment and the retina. However, in the present embodiment, the calibration mirror 36 is used to suitably correct the distance between the anterior segment and the retina at the time of measuring the subject eye E based on the predetermined reference positions $Z_{Ai}$, $Z_{Pi}$. Accordingly, the accurate eye axial length can be calculated in the present embodiment.

(Corresponding Relationships)

The anterior segment light source 12 and the retina light source 62 are respectively examples of "first light source" and "second light source". The anterior segment OCT interferometer 10 and the retinal OCT interferometer 11 are respectively examples of "first interferometer" and "second interferometer". The measurement interference light in the anterior segment OCT measurement and the measurement interference light in the retinal OCT measurement are respectively examples of "first interference light" and "second interference light". The range including the anterior segment and the range including the retina are respectively examples of "first range" and "second range". The refraction measurement optical system 94 is an example of "refractive power measurement optical system". The calibration mirror 36 is an example of "first calibration mirror" and "second calibration mirror".

Second Embodiment

Next, an ophthalmic apparatus 2 of a second embodiment will be described. For the ophthalmic apparatus 2 of the second embodiment, configurations thereof that are the same as those of the ophthalmic apparatus 1 of the first embodiment are given the same reference numbers, and descriptions on operations and processes thereof are omitted.

Figure 18:
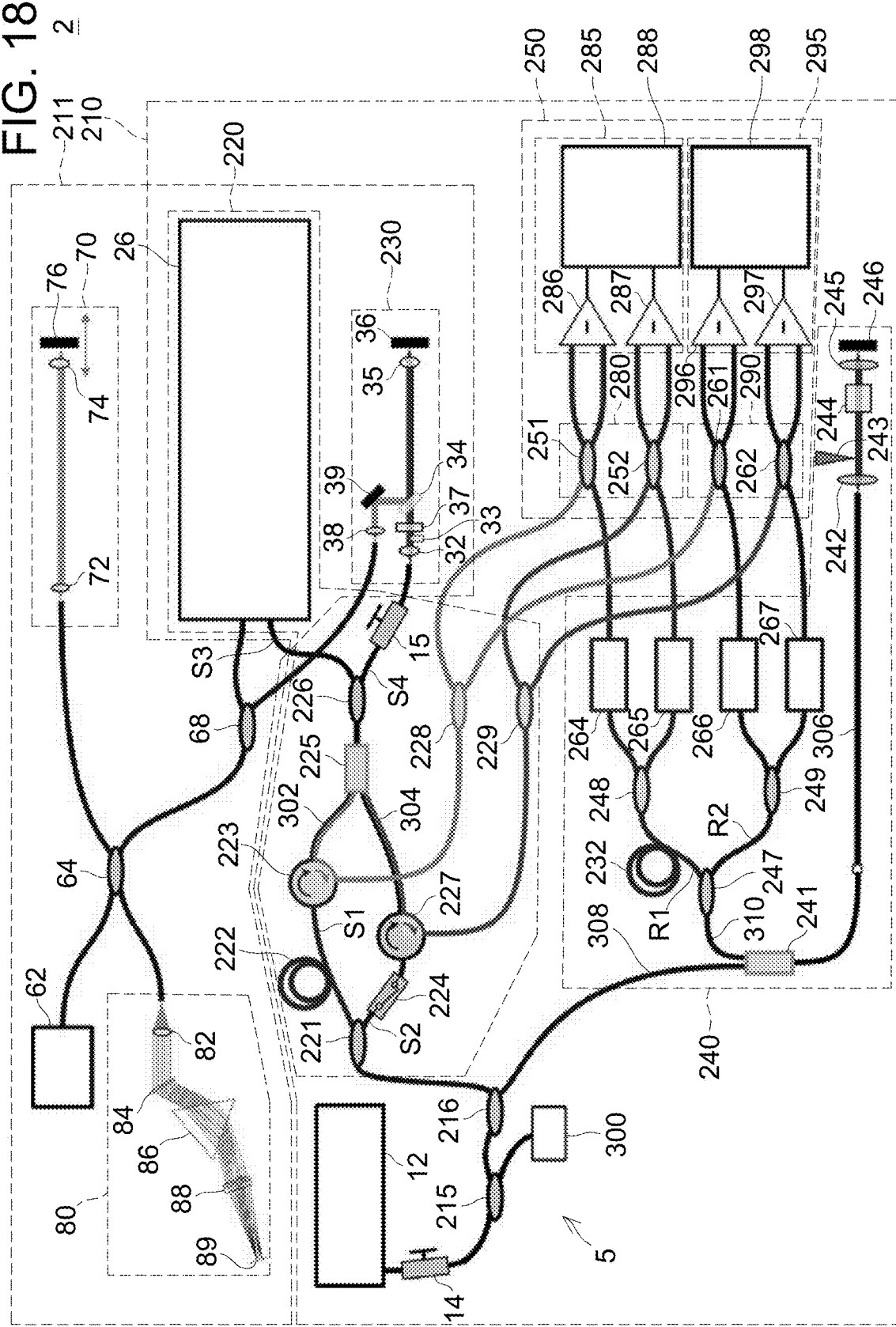
FIG. 18 shows a schematic configuration diagram of an anterior segment OCT interferometer and a retinal OCT interferometer of an ophthalmic apparatus of a second embodiment.

As shown in FIG. 18, the ophthalmic apparatus 2 is provided with an anterior segment OCT interferometer 210 configured to capture tomographic images of the anterior segment of the subject eye E and a retinal OCT interferometer 211 configured to capture tomographic images of the retina of the subject eye E. In the anterior segment OCT interferometer 210, a polarization-sensitive OCT (PS-OCT) that is an optical frequency sweeping OCT using a wavelength-sweeping light source and capable of detecting polarization characteristics of the subject eye E is used. A configuration and control of the retinal OCT interferometer 211 are the same as those of the retinal OCT interferometer 11 of the first embodiment.

As shown in FIG. 18, the anterior segment OCT interferometer 210 is provided with the anterior segment light source 12, a measurement optical system 220, a calibration optical system 230, a reference optical system 240, and an interference optical system 250.

The polarization controller 14 and a fiber coupler 215 are connected to the anterior segment light source 12, and a PMFC (polarization maintaining fiber coupler) 216 and a sampling trigger/clock generator 300 are connected to the fiber coupler 215. As such, the light outputted from the anterior segment light source 12 is inputted to each of the PMFC 216 and the sampling trigger/clock generator 300 through the polarization controller 14 and the fiber coupler 215. The sampling trigger/clock generator 300 is configured to generate sampling triggers and sampling clocks respectively for signal processors 288, 298 (to be described later) by using the light of the anterior segment light source 12.

The measurement optical system 220 is provided with a PMFC 221 connected to the PMFC 216, two measurement optical paths S1, S2 that branch from the PMFC 221, a polarization beam combiner/splitter 225 that connects the two measurement optical paths S1, S2, an SMFC (single mode fiber coupler) 226 connected to the polarization beam combiner/splitter 225, two measurement optical paths S3, S4 that branch from the SMFC 226, and the probe optical system 26 connected to the measurement optical path S3. The calibration optical system 230 is connected to the measurement optical path S4 through a polarization controller 15. An optical path length difference generator 222 and a circulator 223 are disposed on the measurement optical path S1. A MEMS attenuator 224 and a circulator 227 are disposed on the measurement optical path S2. As such, an optical path length difference Δ1 between the measurement optical path S1 and the measurement optical path S2 is generated by the optical path length difference generator 222. The optical path length difference Δ1 may be set longer than a measurement range of the subject eye E in the depth direction. This can suppress interference light that have different optical path length differences from overlapping with each other. As the optical path length difference generator 222, an optical fiber may be used or an optical system such as a mirror or a prism may be used, for example. In the present embodiment, a PM fiber that is 1 m long is used as the optical path length difference generator 222. Further, the measurement optical system 220 is further provided with PMFCs 228, 229. The PMFC 228 is connected to the circulator 223. The PMFC 229 is connected to the circulator 227.

One of the light split at the PMFC 216 (that is, measurement light) is inputted to the above-described measurement optical system 220. The PMFC 221 is configured to split the measurement light inputted from the PMFC 216 into first measurement light and second measurement light. The first measurement light split in the PMFC 221 is guided to the measurement optical path S1 and the second measurement light is guided to the measurement optical path S2. The first measurement guided to the measurement optical path S1 travels through the optical path length difference generator 222 and the circulator 223, and is inputted to the polarization beam combiner/splitter 225. The second measurement guided to the measurement optical path S2 travels through the MEMS attenuator 224 and the circulator 227, and is inputted to the polarization beam combiner/splitter 225. A PM fiber 304 is connected to the polarization beam combiner/splitter 225 in a state of being rotated by 90 degrees in a circumferential direction relative to a PM fiber 302. Due to this, the second measurement light inputted to the polarization beam combiner/splitter 225 is light having a polarization component that is orthogonal to the first measurement light. Since the optical path length difference generator 222 is provided on the measurement optical path S1, the first measurement light is delayed relative to the second measurement light by a distance of the optical path length difference generator 222 (that is, the optical path length difference Δ1 is generated). The polarization beam combiner/splitter 225 is configured to superpose the inputted first measurement light and second measurement light.

The light outputted from the polarization beam combiner/splitter 225 (which is the light in which the first measurement light and the second measurement light are superposed) is inputted to the SMFC 226, and the SMFC 226 splits the inputted light into third measurement light and fourth measurement light. The third measurement light split in the SMFC 226 is guided to the measurement optical path S3 and the fourth measurement light is guided to the measurement optical path S4. The third measurement light guided to the measurement optical path S3 is inputted to the anterior segment OCT optical system 90 of the probe optical system 26 and the subject eye E is irradiated with the light, similar to the above-described first embodiment. Here, an SM (single mode) fiber used in the measurement optical path S3 generates birefringence by stress and bending, so a polarization state of the light provided to the subject eye E may change according to the state of the SM fiber. Reflected light from the subject eye E passes through the anterior segment OCT optical system 90 along the reversed path from its entrance path, is inputted to the SMFC 226, and then is inputted to the polarization beam combiner/splitter 225.

On the other hand, the fourth measurement light guided to the measurement optical path S4 is inputted to the calibration optical system 230 and then is inputted to a glass block 33 through the lens 32. The glass block 33 is disposed such that a part of the fourth measurement light inputted through the lens 32 passes therethrough. For example, as shown in FIG. 18, the glass block 33 is disposed such that substantially a lower half of the fourth measurement light inputted through the lens 32 passes therethrough and substantially an upper half thereof does not pass therethrough. Due to this, a part of the fourth measurement light inputted through the lens 32 (the light traveling on the lower side in FIG. 18) passes through the glass block 33 and is inputted to a quarter wavelength plate 37. On the other hand, the other part of the fourth measurement light inputted through the lens 32 (the light traveling on the upper side in FIG. 18) is inputted to the quarter wavelength plate 37 without passing through the glass block 33. The light inputted to the quarter wavelength plate 37 is given a 90-degrees phase difference when passing through the quarter wavelength plate 37. The light that passed through the quarter wavelength plate 37 is inputted to the calibration mirror 36 through the dichroic mirror 34 and the lens 35. Reflected light from the calibration mirror 36 passes through the lens 35 and is given another 90-degrees phase difference at the quarter wavelength plate 37, and a part of the reflected light passes through the glass block 33 and is inputted to the lens 32 and the other part thereof is inputted to the lens 32 without passing through the glass block 33. Then, the light pass through the lens 32 and are inputted to the SMFC 226. As such, the light that had passes through the glass block 33 and the light that had not passed through the glass block 33 are inputted to the SMFC 226. The light that had passed through the glass block 33 may be light that passed through the glass block 33 once (that is, light that passed through the glass block 33 just once when it traveled from the lens 32 to the lens 35 or when it traveled from the lens 35 to the lens 32), may be light that passed through the glass block 33 twice (that is, light that passed through the glass block 33 when it traveled from the lens 32 to the lens 35 as well as when it traveled from the lens 25 to the lens 32), or may be both of those light. The calibration mirror 36 and the glass block 33 are disposed such that the measurement light that had traveled through the measurement optical path S4 is measured in a vicinity of a Nyquist frequency of measurement range. The light inputted to the SMFC 226 are inputted to the polarization beam combiner/splitter 225. An SM fiber used in the measurement optical path S4 may bend or the temperature thereof may change, which may cause a change in a polarization state of the light traveling in the SM fiber. In the present embodiment, the quarter wavelength plate 37 is suitably rotated to control the polarization state of the light passing through the quarter wavelength plate 37. Due to this, the light can be split in the polarization beam combiner/splitter 225 into polarization components having uniform intensities. That is, intensities of interference signals inputted to balanced light detectors 286, 287, 296, 297 (to be described later) can be uniformized.

The reflected light from the subject eye E and the reflected light from the calibration mirror 36 that were inputted to the polarization beam combiner/splitter 225 are divided in the polarization beam combiner/splitter 225 into two polarization components that perpendicularly intersect each other. For the sake of convenience of explanation, they are herein be termed horizontal polarization reflected light (horizontal polarization component) and vertical polarization reflected light (vertical polarization component). Then, the horizontal polarization reflected light is guided to the measurement light path S1 and the vertical polarization reflected light is guided to the measurement light path S2. The horizontal polarization reflected light has its optical path changed by the circulator 223 and is inputted to the PMFC 228. The PMFC 228 splits the inputted horizontal polarization reflected light, and the split light are respectively inputted to PMFCs 251, 261 of the interference optical system 250 to be described later. Thus, the horizontal polarization reflected light inputted to the PMFCs 251, 261 include the reflected light component from the first measurement light and the reflected light component from the second measurement light. The vertical polarization reflected light has its optical path changed by the circulator 227 and is inputted to the PMFC 229. The PMFC 229 splits the inputted vertical polarization reflected light, and the split light are respectively inputted to PMFCs 252, 262. Thus, the vertical polarization reflected light inputted to the PMFCs 252, 262 include the reflected light component from the first measurement light and the reflected light component from the second measurement light.

The reference optical system 240 includes a polarization beam combiner/splitter 241 connected to the PMFC 216, a reference delay line (242, 243, 244, 245, 246) connected to the polarization beam combiner/splitter 241, a PMFC 247 connected to the polarization beam combiner/splitter 241, two reference optical paths R1 and R2 branching from the PMFC 247, a PMFC 248 connected to the reference light path R1, and a PMFC 249 connected to the reference light path R2. A PM fiber 310 is connected to the polarization beam combiner/splitter 241 in a state of being rotated by 90 degrees in a circumferential direction relative to a PM fiber 308. An optical path length difference generator 232 is provided on the reference light path R1. No optical path length difference generator is provided on the reference light path R2. Therefore, an optical path length difference Δ1' between the reference optical path R1 and the reference optical path R2 is generated by the optical path length difference generator 232. For example, an optical fiber is used for the optical path length difference generator 232. The optical path length difference Δ1' of the optical path length difference generator 232 may be the same as the optical path length difference Δ1 of the optical path length difference generator 222. If the optical path length differences Δ1 and Δ1' are the same, depth positions of a plurality of interference light (to be described later) in the subject coincide with each other. That is, position adjustment for a plurality of acquired tomographic images does not have to be performed.

The other light split in the PMFC 216 (that is, reference light) is inputted to the above-described reference optical system 240. The reference light inputted from the PMFC 216 travels through the polarization beam combiner/splitter 241 and is inputted to the reference delay line (242, 243, 244, 245, 246). The reference delay line (242, 243, 244, 245, 246) is constituted of a lens 242, an attenuator 243, a Faraday rotator 244, a lens 245, and a reference mirror 246. The reference light traveled through the polarization beam combiner/splitter 241 travels through an SM fiber 306, is emitted from a fiber collimator (not shown) and is inputted to the Faraday rotator 244 through the lens 242 and the attenuator 243, for example. When the reference light travels through the Faraday rotator 244, a polarization direction thereof is rotated, for example, by 45 degrees, and the light then is inputted to the reference mirror 246 through the lens 245. The reference light reflected on the reference mirror 246 has its polarization direction rotated again by 45 degrees, enters the fiber collimator, and is inputted to the polarization beam combiner/splitter 241. That is, the light that passed through the reference delay line (242, 243, 244, 245, 246) is inputted to the polarization beam combiner/splitter 241 in a state of having its polarization direction rotated by 90 degrees. Here, the reference mirror 246 is configured to be capable of moving in a direction approaching the lens 242 and in a direction separating from the lens 242. In the present embodiment, a position of the reference mirror 246 is adjusted prior to start of the measurement such that signals from the subject eye E fall within OCT measurement ranges in the depth direction.

Since the reference light that was reflected on the reference mirror 246 and inputted to the polarization beam combiner/splitter 241 has its polarization direction rotated by 90 degrees, it is inputted to the PMFC 247 through the PM fiber 310. The PMFC 247 splits the inputted reference light into first reference light and second reference light. The first reference light is guided to the reference optical path R1 and the second reference light is guided to the reference optical path R2. The first reference light travels through the optical path length difference generator 232 and is inputted to the PMFC 248. The reference light inputted to the PMFC 248 is split into first split reference light and second split reference light. The first split reference light is inputted to the PMFC 251 through a delay line 264. The second split reference light is inputted to the PMFC 252 through a delay line 265. The second reference light is inputted to the PMFC 249 and is split into third split reference light and fourth split reference light. The third split reference light is inputted to the PMFC 261 through a delay line 266. The fourth split reference light is inputted to the PMFC 262 through a delay line 267.

The interference optical system 250 is provided with a first interference light generator 280, a second interference light generator 290, a first interference light detector 285, and a second interference light detector 295.

The first interference light generator 280 includes the PMFCs 251, 252. As described above, the horizontal polarization reflected light from the measurement optical system 220 and the first split reference light (light having the optical path length difference Δ1) from the reference optical system 240 are inputted to the PMFC 251. Here, the horizontal polarization reflected light contains the reflected light component (light having the optical path length difference Δ1) from the first measurement light and the reflected light component (light not having the optical path length difference Δ1) from the second measurement light. Therefore, in the PMFC 251, the reflected light component (light having the optical path length difference Δ1) from the first measurement light of the horizontal polarization reflected light is combined with the first split reference light, by which first interference light (horizontal polarization component) is generated.

The vertical polarization reflected light from the measurement optical system 220 and the second split reference light (light having the optical path length difference Δ1) from the reference optical system 240 are inputted to the PMFC 252. Here, the vertical polarization reflected light contains the reflected light component (light having the optical path length difference Δ1) from the first measurement light and the reflected light component (light not having the optical path length difference Δ1) from the second measurement light. Therefore, in the PMFC 252, the reflected light component (light having the optical path length difference Δ1) from the first measurement light of the vertical polarization reflected light is combined with the second split reference light, by which second interference light (vertical polarization component) is generated.

The second interference light generator 290 includes the PMFCs 261, 262. As described above, the horizontal polarization reflected light from the measurement optical system 220 and the third split reference light (light not having the optical path length difference Δ1) from the reference optical system 240 are inputted to the PMFC 261. Therefore, in the PMFC 261, the reflected light component (light not having the optical path length difference Δ1) from the second measurement light of the horizontal polarization reflected light is combined with the third split reference light, by which third interference light (horizontal polarization component) is generated.

The vertical polarization reflected light from the measurement optical system 220 and the fourth split reference light (light not having the optical path length difference Δ1) from the reference optical system 240 are inputted to the PMFC 262. Therefore, in the PMFC 262, the reflected light component (light not having the optical path length difference Δ1) from the second measurement light of the vertical polarization reflected light is combined with the fourth split reference light, by which fourth interference light (vertical polarization component) is generated. The first interference light and the second interference light correspond to the measurement light that has passed through the measurement optical path S1, and the third interference light and the fourth interference light correspond to the measurement light that has passed through the measurement optical path S2.

The first interference light detector 285 is configured to detect the interference light generated by the first interference light generator 280 (the first interference light and the second interference light). The second interference light detector 295 is configured to detect the interference light generated by the second interference light generator 290 (the third interference light and the fourth interference light).

The first interference light detector 285 includes the balanced light detectors 286, 287 (which may simply be termed detectors 286, 287 hereinbelow) and the signal processor 288 connected to the detectors 286, 287. The PMFC 251 is connected to input terminals of the detector 286, and the signal processor 288 is connected to an output terminal of the detector 286. The PMFC 251 splits the first interference light into two interference light having phases different from each other by 180 degrees, and the two interference light are respectively inputted to the input terminals of the detector 286. The detector 286 performs differential amplification processing and noise reduction processing on the two interference light having phases different from each other by 180 degrees inputted from the PMFC 251 to convert them into an electric signal (first interference signal) and outputs the first interference signal to the signal processor 288. That is, the first interference signal is an interference signal HH between the reference light and the horizontal polarization reflected light from the subject eye E and the calibration mirror 36 based on the horizontal polarization measurement light. Similarly, the PMFC 252 is connected to input terminals of the detector 287, and the signal processor 288 is connected to an output terminal of the detector 287. The PMFC 252 splits the second interference light into two interference light having phases different from each other by 180 degrees, and the two interference light are respectively inputted to the input terminals of the detector 287. The detector 287 performs differential amplification processing and noise reduction processing on the two interference light having phases different from each other by 180 degrees to converted them into an electric signal (second interference signal) and outputs the second interference signal to the signal processor 288. That is, the second interference signal is an interference signal HV between the reference light and the vertical polarization reflected light from the subject eye E and the calibration mirror 36 based on the horizontal polarization measurement light.

The signal processor 288 is configured to sample the first interference signal and the second interference signal based on the sampling trigger and the sampling clock inputted from the sampling trigger/clock generator 300. The first and second interference signals sampled in the signal processor 288 are inputted to a processor 400 to be described later. A known data acquisition device (a so-called DAQ) may be used as the signal processor 288.

Similarly to the first interference light detector 285, the second interference light detector 295 includes the balanced light detectors 296, 297 (which may simply be termed detectors 296, 297 hereinbelow) and the signal processor 298 connected to the detectors 296, 297. The PMFC 261 is connected to input terminals of the detector 296, and the signal processor 298 is connected to an output terminal of the detector 296. The PMFC 261 splits the third interference light into two interference light having phases different from each other by 180 degrees, and inputs the two interference light respectively to the input terminals of the detector 296. The detector 296 performs differential amplification processing and noise reduction processing on the two interference light having phases different from each other by 180 degrees to convert them into an electric signal (third interference signal) and outputs the third interference signal to the signal processor 298. That is, the third interference signal is an interference signal VH between the reference light and the horizontal polarization reflected light from the subject eye E and the calibration mirror 36 based on the vertical polarization measurement light. Similarly, the PMFC 262 is connected to input terminals of the detector 297, and the signal processor 298 is connected to an output terminal of the detector 297. The PMFC 262 splits the fourth interference light into two interference light having phases different from each other by 180 degrees, and inputs the two interference light respectively to the input terminals of the detector 297. The detector 297 performs differential amplification processing and noise reduction processing on the two interference light having phases different from each other by 180 degrees to convert them into an electric signal (fourth interference signal) and outputs the fourth interference signal to the signal processor 298. That is, the fourth interference signal is an interference signal VV between the reference light and the vertical polarization reflected light from the subject eye E and the calibration mirror 36 based on the vertical polarization measurement light.

The signal processor 298 is configured to sample the third interference signal and the fourth interference signal based on the sampling trigger and the sampling clock inputted from the sampling trigger/clock generator 300. The third interference signal and the fourth interference signal sampled in the signal processor 298 are inputted to the processor 400 to be described later. A known data collection device (a so-called DAQ) may be used as the signal processor 298. According to this configuration, the interference signals that represent four polarization characteristics of the subject eye E can be acquired.

Figure 19:
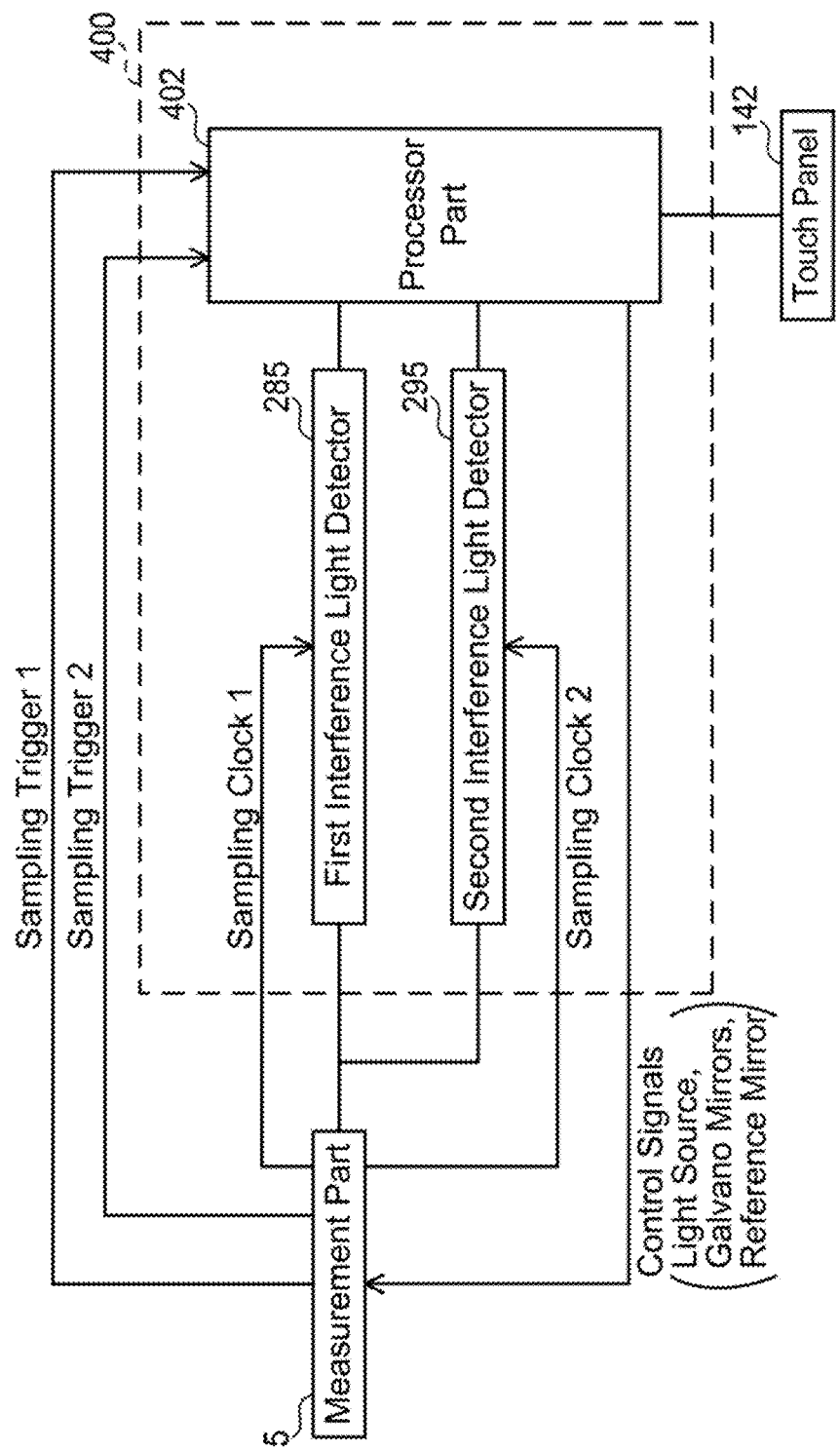
FIG. 19 is a diagram showing a control system of the ophthalmic apparatus of the second embodiment.

Next, a configuration of a control system of the ophthalmic apparatus 2 according to the present embodiment will be described with reference to FIG. 19. As shown in FIG. 19, the ophthalmic apparatus 2 is controlled by the processor 400. The processor 400 includes a processor part 402, the first interference light detector 285, and the second interference light detector 295. The first interference light detector 285, the second interference light detector 295, and the processor part 402 are connected to a measurement part 5. The processor part 402 is configured to output a control signal to the measurement part 5 to drive the scanner 106, thereby moving the incidence position of the measurement light to the anterior segment of the subject eye E. The first interference light detector 285 is configured to acquire first sampling data with respect to the interference signals (the interference signal HH and the interference signal HV) inputted from the measurement part 5, based on a sampling clock 1 inputted from the measurement part 5 and by using a sampling trigger 1 as a trigger, and output the first sampling data to the processor part 402. The processor part 402 performs calculation processing such as Fourier transform processing on the first sampling data to generate an HH tomographic image and an HV tomographic image. The second interference light detector 295 is configured to acquire second sampling data with respect to the interference signals (the interference signal VH and the interference signal VV) inputted from the measurement part 5, based on a sampling clock 2 inputted from the measurement part 5 and by using a sampling trigger 2 as a trigger, and output the second sampling data to the processor part 402. The processor part 402 performs calculation processing such as Fourier transform processing on the second sampling data to generate a VH tomographic image and a VV tomographic image. Here, the HH tomographic image, the VH tomographic image, the HV tomographic image, and the VV tomographic image are tomographic images at the same position. Therefore, the processor part 402 can generate tomographic images having four polarization characteristics (HH, HV, VH, VV) that represent a Jones matrix of the subject eye E.

Figure 20:
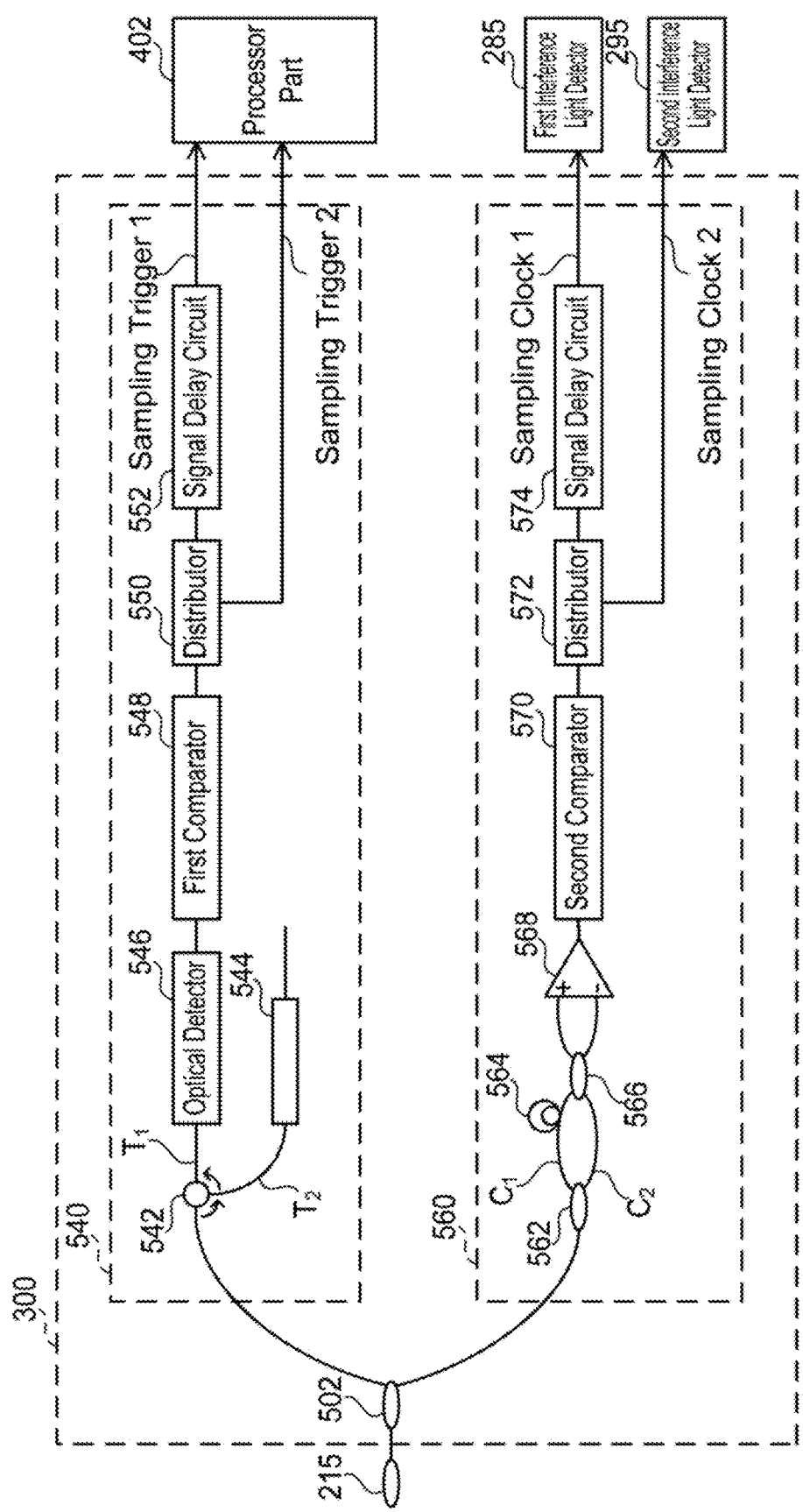
FIG. 20 is a diagram showing a configuration of a sampling trigger/clock generator.

As shown in FIG. 20, the sampling trigger/clock generator 300 includes a fiber coupler 502, a sampling trigger generator (540 to 552), and a sampling clock generator (560 to 574). The light from the anterior segment light source 12 is inputted, through the fiber coupler 215 and the fiber coupler 502, to each of the sampling trigger generator 540 and the sampling clock generator 560.

The sampling trigger generator 540 may generate a sampling trigger by using, for example, an FBG (Fiber Bragg Grating) 544. As shown in FIG. 20, the FBG 544 reflects only a specific wavelength of the light inputted from the anterior segment light source 12, thereby generating a sampling trigger. The generated sampling trigger is inputted to a distributor 550. The distributor 550 distributes the sampling trigger into the sampling trigger 1 and the sampling trigger 2. The sampling trigger 1 is inputted, through a signal delay circuit 552, to the processor part 402. The sampling trigger 2 is directly inputted to the processor part 402. The sampling trigger 1 is a trigger signal for the interference signals (the first interference signal and the second interference signal) inputted from the first interference light detector 285 to the processor part 402. The sampling trigger 2 is a trigger signal for the interference signals (the third interference signal and the fourth interference signal) inputted from the second interference light detector 295 to the processor part 402. The signal delay circuit 552 is designed so that the sampling trigger 1 is delayed relative to the sampling trigger 2 by a time corresponding to the optical path length difference $\Delta 1$ of the optical path length difference generator 222. Thus, frequency at which sampling of the interference signals inputted from the first interference light detector 285 is started can be made equal to frequency at which sampling of the interference signals inputted from the second interference light detector 295 is started. Here, only the sampling trigger 1 may be generated. Since the optical path length difference $\Delta 1$ is already known, upon sampling the interference signals inputted from the second interference light detector 295, the sampling may be started with a delay from the sampling trigger 1 by a time corresponding to the optical path length difference $\Delta 1$.

The sampling clock generator 560 may be constituted of a Mach-Zehnder interferometer, for example. As shown in FIG. 20, the sampling clock generator 560 generates a sampling clock with an equal frequency, by using the Mach-Zehnder interferometer. The sampling clock generated by the Mach-Zehnder interferometer is inputted to a distributor 572. The distributor 572 distributes the sampling clock into the sampling clock 1 and the sampling clock 2. The sampling clock 1 is inputted, through a signal delay circuit 574, to the first interference light detector 285. The sampling clock 2 is directly inputted to the second interference light detector 295. The signal delay circuit 574 is designed so as to cause a delay by a time corresponding to the optical path length difference $\Delta 1$ of the optical path length difference generator 222. Thus, the interference light with the delay corresponding to the optical path length difference generator 222 can also be sampled at the same timing. Thus, misalignment among the positions in a plurality of acquired tomographic images can be prevented. In the present embodiment, the Mach-Zehnder interferometer is used for generating the sampling clocks. Alternatively, for generating the sampling clocks, a Michelson interferometer may be used or an electric circuit may be used. Alternatively, the sampling clocks may be generated by using a light source having a sampling clock generator as the anterior segment light source 12.

In the ophthalmic apparatus 2 of the present embodiment, when the plural types of measurements are executed on the subject eye E, the depth positions of respective parts of the anterior segment and the retina and the eye axial length can be measured by executing processes similar to those of the first embodiment (see FIG. 6, etc.). As above, even in the case where the PS-OCT is used as the anterior segment OCT interferometer 210, the plural types of measurements on the subject eye E can be executed with high accuracy and efficiency. When the anterior segment and the retina are measured simultaneously in the ophthalmic apparatus 2, the first measurement light may be set as the only light outputted from the polarization beam combiner/splitter 225 by adjusting the MEMS attenuator 224 to set quantity of light that passes through the MEMS attenuator 224 to zero. In this case, the quantity of light provided to the subject eye E from the anterior segment OCT interferometer 210 becomes substantially halved, and thus the quantity of light which the retinal OCT interferometer 211 can provide to the subject eye E can be increased within a light quantity range that can be provided to the subject eye E under the safety standard. Further, in this case, the optical signals are detected only in the detectors 286, 296 in the anterior segment OCT measurement, and taking an average of tomographic images acquired from these signals can ensure acquisition of the interference signals, independently from the polarization state of the light that is backscattered from the subject eye E.

(Variants)

The above-described embodiments exemplify the examinations for the ranges including the anterior segment and the retina of the subject eye E, however, they are not limited thereto. For example, ranges including the other parts of the subject eye E may be examined by suitably adjusting the central wavelengths of the light outputted from the light sources 12, 62 and/or by suitably changing the configuration of the probe optical system 26.

Further, in the above-described embodiments, in the case where the condition under which the fringe washout occurs in the retinal OCT interferometer 11 is satisfied (that is, in the case of scan resolution>optical resolution), the light is outputted in pulses from the retina light source 62. However, the light may be outputted in pulses from the retina light source 62 even in a case where the condition under which the fringe washout occurs is not satisfied, or the light may be outputted continuously from the retina light source 62 even in the case where the condition under which the fringe washout occurs is satisfied, if there is no influence on the accuracy of the acquired tomographic images. The light of the anterior segment light source 12 may be outputted in pulses in the anterior segment OCT measurement.

Further, in the above-described embodiments, the light is outputted in pulses from the retina light source 62 at the predetermined duty cycle and with the predetermined period to suppress the fringe washout. However, as an alternative to the above configuration, the interference light obtained from the retina of the subject eye E may be detected at a predetermined duty cycle and with a predetermined period while the retina light source 62 continuously outputs the light. That is, a detection term during which the interference light is detected and a no-detection term during which the interference light is not detected may be set, and the detection term may be set with a period according to the A-scan speed of the retinal OCT measurement. Specifically, for example, the interference light may be detected in pulses to satisfy the values of the above-described embodiments (that is, the duty cycle of less than 10000/27036 and the period of 100 µs). In the case where the light is outputted in pulses from the retina light source 62, characteristics of the light may become unstable. However, according to such a configuration, the characteristics of the light outputted from the retina light source 62 are stabilized, and the fringe washout can suitably be suppressed.

Further, the eye axial length of a subject eye to be examined generally differs depending on the subject. Due to this, depending on an initial setting of the optical path length in the retinal OCT measurement, the interference light reflected from the retina may fall outside of a retinal OCT capturing range. As a result, tomographic images of the retina may not be captured and the correction of the distance from the anterior segment to the retina by the calibration mirror 36 may be difficult. In such a case, firstly, the optical path length from the retina light source 62 to the calibration mirror 36 may be adjusted so that the signals of the interference light reflected from the retina fall within the capturing range. For example, assuming that a shift amount in the depth direction from the initial setting of the capturing range is $Z_{PREF}$, an optical path length difference L' of the reference position $Z_{Ai}$ and the reference position $Z_{Pi}$ having considered the shift in the depth direction can be calculated as $L'=L_i-Z_{PREF}$. As such, the eye axial length of the subject eye E can suitably be calculated by changing the capturing range in the retinal OCT measurement and calculating displacement in the optical path length differences at the respective reference positions of the calibration mirror 36 accompanying that change.

In the above-described embodiments, the refraction measurement optical system 94 is provided with the perforated mirror 105 disposed between the dichroic mirror 104 and the scanner 106, and the ring lens 136 disposed between the lens 134 and the sensor 138. However, for example, the refraction measurement optical system 94 may be provided with a half mirror instead of the perforated mirror 105, and may be provided with a lens array including a large number of fine lenses arranged in a matrix instead of the ring lens 136. In such a configuration, the reflected light from the subject eye E is split by the half mirror, and substantially a half of the reflected light is reflected on the half mirror. The light reflected on the half mirror is inputted to the lens array. When the light enters the lens array, the large number of fine lenses in the lens array provides light in the same number as the lenses to the sensor 138. When light having a distorted wave surface enters the lens array, the lens, among the large number of fine lenses, at a position corresponding to a distorted position provides light with its optical axis displaced to the sensor 138. That is, by disposing the lens array between the lens 134 and the sensor 138, a function equivalent to that of an optical system of a wave surface sensor can be given to the refraction measurement optical system 94. Due to this, the refraction measurement optical system 94 can measure not only the total refractive power of the subject eye E but also a total aberration of the subject eye E, and information related to refraction of the subject eye E can be measured at a greater detail.

Further, in the above-described embodiments, the refraction measurement (S14) is executed prior to the anterior segment OCT measurement and the retinal OCT measurement (S18 of FIG. 6). However, the refraction measurement may be executed simultaneously with the retinal OCT measurement by using the light outputted from the retina light source 62. For example, in the case where the subject had previously taken the refraction measurement and the OCT measurement, the anterior segment OCT measurement, the retinal OCT measurement, and the refraction measurement on the subject eye E can be executed simultaneously by adjusting the probe optical system 26 based on the results of the previous measurements. In such a configuration, the efficiency of the examinations of the subject eye E is further improved. Alternatively, the refraction measurement may not be executed. In this case, S14 may be omitted.

Further, in the above-described embodiments, the light outputted from the retina light source 62 is used in the measurement of the refractive power of the subject eye E. However, a light source different from the retina light source 62 may be used for the measurement of the refractive power of the subject eye E. In this case, the different light source may output light with a wavelength that differs from those of the light outputted from the anterior segment light source 12 and the retina light source 62, and for example, it may output light with a central wavelength of 0.70 µm or more and 0.95 µm or less. The light with the wavelength of 0.70 µm or more and 0.95 µm or less has a high intraocular penetration rate. Further, the light with the wavelength of 0.70 µm or more and 0.95 µm or less has a low relative visibility to the subject eye E, so the light is less likely to make the subject feel brightness as well as is suitable for visual function evaluation because it is close to visible light. As such, by using the light with the wavelength of 0.70 µm or more and 0.95 µm or less in the measurement of the refractive power, the light from the light source can sufficiently be provided to the retina of the subject eye E and the light with the suitable wavelength for measuring the refractive power of the subject eye E can be outputted.

Further, in the above-described embodiments, the same calibration mirror 36 is used to correct the distance from the anterior segment to the retina. However, each of the anterior segment OCT interferometer 10 and the retinal OCT interferometer 11 may be provided with a calibration mirror.

Specific examples of the disclosure herein have been described in detail, however, these are mere exemplary indications and thus do not limit the scope of the claims. The art described in the claims includes modifications and variations of the specific examples presented above. Technical features described in the description and the drawings may technically be useful alone or in various combinations, and are not limited to the combinations as originally claimed.

What is claimed is:

1. An ophthalmic apparatus comprising:
   a first light source configured to output first light with which a subject eye is irradiated;
   a second light source configured to output second light with which the subject eye is irradiated;
   a first interferometer configured to execute an examination of a first range of the subject eye using first interference light which is obtained from reflected light of the first light;
   a second interferometer configured to execute an examination of a second range of the subject eye using second interference light which is obtained from reflected light of the second light, the second range being different from the first range; and
   a scanner disposed on an overlapping optical path where the first optical path and the second optical path overlap, and configured to scan the first light outputted from the first light source and scan the second light outputted from the second light source,
   wherein a central wavelength of the first light is different from a central wavelength of the second light, a first optical path and a second optical path at least partially overlap with each other, the first optical path being an optical path of the first light, and the second optical path being an optical path of the second light, the examination of the first range and the examination of the second range are able to be executed simultaneously, and the second light source is configured to output the second light in pulses when a scan resolution in the examination of the second range is lower than an optical resolution in the examination of the second range.

2. The ophthalmic apparatus according to claim 1, wherein the first range includes an anterior segment of the subject eye, and the second range includes a retina of the subject eye.

3. The ophthalmic apparatus according to claim 1, wherein the central wavelength of the first light is longer than the central wavelength of the second light;

the central wavelength of the first light outputted from the first light source is 0.95 μm or more and 1.80 μm or less, and the central wavelength of the second light outputted from the second light source is 0.40 μm or more and 1.15 μm or less.

4. The ophthalmic apparatus according to claim 1, wherein the second light source is configured to continuously output the second light when a scan resolution in the examination of the second range is higher than an optical resolution in the examination of the second range.

5. The ophthalmic apparatus according to claim 4, further comprising:

an objective lens disposed on the overlapping optical path and disposed between the scanner and the subject eye, wherein the scanner comprises a mirror which changes traveling directions of the first light and the second light to a predetermined direction, and the second light source is configured to continuously output the second light when the following formula is satisfied:

$(Fp \cdot \lambda p \cdot Mp)/Dp > (\pi/4) \cdot (Ma/f_{obj}) \cdot (Wa/Na) \cdot Fa$ (wherein in the examination of the first range: Fa is an A-scan speed; Wa is a scan range in a first direction orthogonal to a depth direction of the subject eye; Na is a number of times of A-scans within the scan range in the first direction; and Ma is a magnification of the mirror, and wherein in the examination of the second range: Fp is an A-scan speed; and Mp is a magnification of the mirror, wherein λp is the central wavelength of the second light, Dp is a beam diameter of the second light, and $f_{obj}$ is a focal length of the objective lens).

6. The ophthalmic apparatus according to claim 1, further comprising:

an objective lens disposed on the overlapping optical path and disposed between the scanner and the subject eye, wherein the scanner comprises a mirror which changes traveling directions of the first light and the second light to a predetermined direction, and the second light source is configured to output the second light in pulses when the following formula is satisfied:

$(Fp \cdot \lambda p \cdot Mp)/Dp < (\pi/4) \cdot (Ma/f_{obj}) \cdot (Wa/Na) \cdot Fa$ (wherein in the examination of the first range: Fa is an A-scan speed; Wa is a scan range in a first direction orthogonal to a depth direction of the subject eye; Na is a number of times of A-scans within the scan range in the first direction; and Ma is a magnification of the mirror, and wherein in the examination of the second range: Fp is an A-scan speed; Mp is a magnification of the mirror, wherein λp is the central wavelength of the second light; Dp is a beam diameter of the second light; and $f_{obj}$ is a focal length of the objective lens).

7. The ophthalmic apparatus according to claim 6, wherein the second light source is configured to output the second light in pulses with a period 1/Fp such that a duty cycle D satisfies the following formula:

$D < Fp/\{\pi/(4\lambda p) \cdot (Dp/f_{obj}) \cdot (Ma/Mp) \cdot (Wa/Na) \cdot Fa\}$.

8. The ophthalmic apparatus according to claim 1, further comprising:

an objective lens disposed on the overlapping optical path and disposed between the scanner and the subject eye, wherein the scanner comprises a mirror which changes traveling directions of the first light and the second light to a predetermined direction, and the second interferometer is configured to detect the second light in pulses with a period 1/Fp such that a duty cycle D satisfies the following formula:

$D < Fp/\{\pi/(4\lambda p) \cdot (Dp/f_{obj}) \cdot (Ma/Mp) \cdot (Wa/Na) \cdot Fa\}$ (wherein in the examination of the first range: Fa is an A-scan speed; Wa is a scan range in a first direction orthogonal to a depth direction of the subject eye; Na is a number of times of A-scans within the scan range in the first direction; and Ma is a magnification of the mirror, wherein in the examination of the second range: Fp is an A-scan speed; and Mp is a magnification of the mirror, wherein λp is the central wavelength of the second light, Dp is a beam diameter of the second light, and $f_{obj}$ is a focal length of the objective lens).

9. The ophthalmic apparatus according to claim 1, further comprising:

a refractive power measurement optical system configured to measure refractive power of the subject eye using the second light outputted from the second light source.

10. The ophthalmic apparatus according to claim 1, wherein the first range includes an anterior segment of the subject eye, the second range includes a retina of the subject eye, the ophthalmic apparatus further comprises:

a processor storing a distance from the first range to the second range that is measured in advance; and a memory storing computer-readable instructions therein, wherein the computer-readable instructions, when executed by the processor, cause the processor to:

calculate a shape of the anterior segment of the subject eye based on the first interference light and calculate a shape of the retina of the subject eye based on the second interference light; and calculate an eye axial length of the subject eye based on the calculated shape of the anterior segment, the calculated shape of the retina, and the distance from the first range to the second range.

11. The ophthalmic apparatus according to claim 10, wherein
the first interferometer comprises a first calibration mirror,
the second interferometer comprises a second calibration mirror,
the processor stores a first reference position of the first calibration mirror, a second reference position of the second calibration mirror, and a distance from the first reference position to the second reference position, the first reference position and the second reference position being predetermined, and
the computer-readable instructions, when executed by the processor, cause the processor to:
calculate a first displacement amount between a current position of the first calibration mirror and the first reference position when calculating the shape of the anterior segment;
calculate a second displacement amount between a current position of the second calibration mirror and the second reference position when calculating the shape of the retina; and
correct the distance from the first range to the second range based on the first displacement amount and the second displacement amount when calculating the eye axial length.

12. An ophthalmic apparatus comprising:
a first light source configured to output first light with which a subject eye is irradiated;
a second light source configured to output second light with which the subject eye is irradiated;
a first interferometer configured to execute an examination of a first range of the subject eye using first interference light which is obtained from reflected light of the first light;
a second interferometer configured to execute an examination of a second range of the subject eye using second interference light which is obtained from reflected light of the second light, the second range being different from the first range; and
a scanner disposed on an overlapping optical path where the first optical path and the second optical path overlap, and configured to scan the first light outputted from the first light source and scan the second light outputted from the second light source,
wherein
a central wavelength of the first light is different from a central wavelength of the second light,
a first optical path and a second optical path at least partially overlap with each other, the first optical path being an optical path of the first light, and the second optical path being an optical path of the second light, and
the examination of the first range and the examination of the second range are able to be executed simultaneously,
the ophthalmic apparatus further comprises an objective lens disposed on the overlapping optical path and disposed between the scanner and the subject eye, wherein
the scanner comprises a mirror which changes traveling directions of the first light and the second light to a predetermined direction, and
the second interferometer is configured to detect the second light in pulses with a period 1/Fp such that a duty cycle D satisfies the following formula:

$$D < Fp / \{\pi/(4\lambda p) \cdot (Dp/f_{obj}) \cdot (Ma/Mp) \cdot (Wa/Na) \cdot Fa\}$$

(wherein in the examination of the first range: Fa is an A-scan speed; Wa is a scan range in a first direction orthogonal to a depth direction of the subject eye; Na is a number of times of A-scans within the scan range in the first direction; and Ma is a magnification of the mirror, wherein in the examination of the second range: Fp is an A-scan speed; and Mp is a magnification of the mirror, wherein $\lambda p$ is the central wavelength of the second light, Dp is a beam diameter of the second light, and $f_{obj}$ is a focal length of the objective lens).

13. An ophthalmic apparatus comprising:
a first light source configured to output first light with which a subject eye is irradiated;
a second light source configured to output second light with which the subject eye is irradiated;
a first interferometer configured to execute an examination of a first range of the subject eye using first interference light which is obtained from reflected light of the first light; and
a second interferometer configured to execute an examination of a second range of the subject eye using second interference light which is obtained from reflected light of the second light, the second range being different from the first range,
wherein
a central wavelength of the first light is different from a central wavelength of the second light,
a first optical path and a second optical path at least partially overlap with each other, the first optical path being an optical path of the first light, and the second optical path being an optical path of the second light,
the examination of the first range and the examination of the second range are able to be executed simultaneously, and
the ophthalmic apparatus further comprises a refractive power measurement optical system configured to measure refractive power of the subject eye using the second light outputted from the second light source.

14. An ophthalmic apparatus comprising:
a first light source configured to output first light with which a subject eye is irradiated;
a second light source configured to output second light with which the subject eye is irradiated;
a first interferometer configured to execute an examination of a first range of the subject eye using first interference light which is obtained from reflected light of the first light; and
a second interferometer configured to execute an examination of a second range of the subject eye using second interference light which is obtained from reflected light of the second light, the second range being different from the first range,
wherein
a central wavelength of the first light is different from a central wavelength of the second light,
a first optical path and a second optical path at least partially overlap with each other, the first optical path being an optical path of the first light, and the second optical path being an optical path of the second light, and the examination of the first range and the examination of the second range are able to be executed simultaneously,
wherein
the first range includes an anterior segment of the subject eye,
the second range includes a retina of the subject eye,
the ophthalmic apparatus further comprises:
- a processor storing a distance from the first range to the second range that is measured in advance; and
- a memory storing computer-readable instructions therein, wherein the computer-readable instructions, when executed by the processor, cause the processor to:
  - calculate a shape of the anterior segment of the subject eye based on the first interference light and calculate a shape of the retina of the subject eye based on the second interference light; and
  - calculate an eye axial length of the subject eye based on the calculated shape of the anterior segment, the calculated shape of the retina, and the distance from the first range to the second range.

\* \* \* \* \*